US006417183B1

(12) United States Patent
Keith et al.

(10) Patent No.: US 6,417,183 B1
(45) Date of Patent: Jul. 9, 2002

(54) 1,4-DIAZACYCLOHEPTANE DERIVATIVES

(75) Inventors: Richard A Keith; Edward J Warawa; Thomas R Simpson, all of Wilmington, DE (US)

(73) Assignee: Astrazenela UK Limited (GB)

( * ) Notice: Subject to any disclaimer, the term of this patent is extended or adjusted under 35 U.S.C. 154(b) by 0 days.

(21) Appl. No.: 09/581,615

(22) PCT Filed: Dec. 15, 1998

(86) PCT No.: PCT/GB98/06378

§ 371 (c)(1),
(2), (4) Date: Jun. 15, 2000

(87) PCT Pub. No.: WO99/32461

PCT Pub. Date: Jul. 1, 1999

(30) Foreign Application Priority Data

Dec. 18, 1997 (GB) ............................................... 9726736

(51) Int. Cl.$^7$ ...................... A61K 31/55; C07D 243/08; A61P 25/28

(52) U.S. Cl. ........................................ 514/218; 540/575
(58) Field of Search ........................... 514/218; 540/575

(56) References Cited

U.S. PATENT DOCUMENTS 5,026,707 A * 6/1991 Nixon et al. ................ 514/255

FOREIGN PATENT DOCUMENTS

| WO | WO 97/31887 | 9/1997 |
| WO | WO 98/00412 | 1/1998 |

OTHER PUBLICATIONS

Zech et al., Novel Sites for Phenylalkylamines: Characterisation of a Sodium–Sensitive Drug Receptor with (−)–[.superscript.3H]emopamil, European Journal of Pharmacology– Molecular Pharmacology Section, vol. 208, No. 2, pp. 119–130, Oct. 14, 1991.*

Evans J M et al: "Synthesis and Antihypertensive Activity of 6,7–Disubstituted Trans–4–Amino–3–4–Dihydro–2, 2–Dimethyl–2H–1–Benzopyran–3–Ols" Journal of Medicinal Chemistry. vol. 27, No. 9, 1984, pp. 1127–1131, XP002048426 see the whole document.

* cited by examiner

Primary Examiner—Brenda Coleman
(74) Attorney, Agent, or Firm—Kenneth F. Mitchell

(57) ABSTRACT

This invention provides substituted 1,2,3,4-tetrahydronaphthalene [$^3$H]-emopamil binding site inhibitors useful in the treatment of neurological disorders. Such inhibitors are compounds of formula (I)

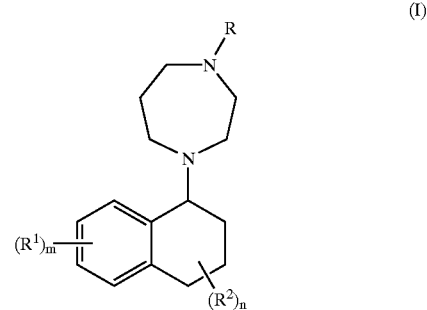

(I)

wherein R, R1, m, R2 and n are as defined in the specification. The invention also provides pharmaceutical compositions containing such compounds, methods of using such compounds and methods of making such compounds

11 Claims, No Drawings

1,4-DIAZACYCLOHEPTANE DERIVATIVES

This is a national stage application under 35 U.S.C. §317 of PCT/GB98/03768, filed Dec. 15, 1998.

The present invention relates to chemical compounds, in particular 1,4-diazacycloheptanes, to processes for their preparation and to chemical intermediates useful in such processes. The present invention further relates to 1,4-diazacycloheptanes, to pharmaceutical compositions containing them and to their use in methods of therapeutic treatment of animals including man, in particular in the treatment of neurological disorders.

Neurological disorders, for which the present compounds are useful, include stroke, head trauma, transient cerebral ischemic attack, and chronic neurodegenerative disorders such as Alzheimer's disease, Parkinson's disease, diabetic neuropathy, amyotrophic lateral sclerosis, multiple sclerosis, vascular dementia and AIDS-related dementia.

The compounds useful in the present invention are believed to act by binding with the [$^3$H]-emopamil binding site. Emopamil has classically been thought of as a neuroprotective agent whose efficacy is most likely derived from actions at either voltage-sensitive calcium channels (VSCC) or 5-HT$_2$ receptors. An apparent paradox to this logic is that verapamil, although chemically and pharmacologically very similar to emopamil, is not neuroprotective. While the lack of neuroprotective efficacy by verapamil was initially explained by lack of CNS penetration, recent studies suggest other factors may be involved (Keith et al., Br. J. Pharmacol. 113: 379–384, 1994).

[$^3$H]-Emopamil binding defines a unique high affinity site that is not related to VSCC, is found in the brain, but is most prevalent in the liver (Moebius et al., Mol. Pharmacol. 43: 139–148, 1993). Moebius et al. have termed this the "anti-ischemic" binding site on the basis of high affinity displacement by several chemically disparate neuroprotective agents. In liver, the [$^3$H]-emopamil binding site is localized to the endoplasmic reticulum.

Neuroprotective compounds are known, for example emopamil and ifenprodil, that exhibit high affinity for the [$^3$H]-emopamil binding site. However these are not selective inhibitors and exhibit activity either at neuronal VSCC, the polyamine site of the NMDA receptor (N-Methyl-D-aspartate) and/or the sigma-1 binding site. We have now found a class of compounds that show selective action at the [$^3$H]-emopamil binding site that are neuroprotective in global and focal models of cerebral ischemia without acting directly at either VSCC or NMDA receptors, and consequently exhibit fewer associated side effects than are conventionally seen with either emopamil (hypotension) or ifenprodil (behavioural manifestations). Such compounds are especially useful in treating neurodegeneration resulting from ischemia, for example in Alzheimer's disease, vascular dementia, Parkinson's disease, Huntington's disease and AIDS-related dementia. In another aspect such compounds are especially useful in treating stroke as they provide neuronal protection by preventing neuronal death in the penumbra region surrounding the core infarct. Accordingly the present invention provides the use of a compound which binds selectively to the [$^3$H]-emopamil binding site for treating neurodegeneration resulting from ischemia.

Accordingly the present invention provides a compound of the formula (I):

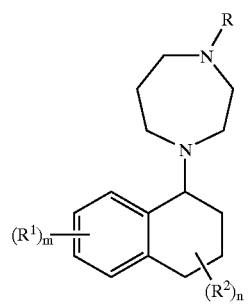

(I)

wherein:
R is hydrogen, $C_{1-10}$alkyl, $C_{3-8}$cycloalkyl, $C_{3-8}$cycloalkyl$C_{1-6}$alkyl, phenyl$C_{1-6}$alkyl or phenyl;
$R^1$ is $C_{1-6}$alkyl, $C_{2-6}$alkenyl, $C_{1-6}$alkoxy, halo, hydroxy, $C_{1-6}$alkanoyl, halo$C_{1-6}$alkyl, cyano or nitro;
m is 0, 1 or 2;
$R^2$ is $C_{1-6}$alkyl;
n is 1, 1 or 2;
wherein any phenyl ring is optionally substituted; p1 or a pharmaceutically acceptable salt or in vivo hydrolysable ester, amide or carbanate thereof Any phenyl ring in R may be optionally substituted, for example by up to five substituents, preferably up to three substituents which may be the same or different. Typical substituents include: hydroxy; $C_{1-6}$alkoxy for example methoxy; mercapto; $C_{1-6}$alkylthio for example methylthio; amino; $C_{1-6}$alkylamino for example methylamino; di-($C_{1-6}$alkyl)amino for example dimethylamino; carboxy; carbamoyl; $C_{1-6}$alkylcarbamoyl for example methylcarbamoyl; di-$C_{1-6}$alkylcarbamoyl for example dimethylcarbamoyl; $C_{1-6}$alkylsulphonyl for example methylsulphonyl; arylsulphonyl for example phenylsulphonyl; $C_{1-6}$alkylaminosulphonyl for example methylaminosulphonyl; di-($C_{1-6}$alkyl)aminosulphonyl for example dimethylamino-sulphonyl; nitro; cyano; cyano-$C_{1-6}$alkyl for example cyanomethyl; hydroxy$C_{1-6}$alkyl for example hydroxymethyl; amino-$C_{1-6}$alkyl for example aminoethyl; $C_{1-6}$alkanoyl-amino for example acetamido; $C_{1-6}$alkoxycarbonylamino for example methoxycarbonylamino; $C_{1-6}$alkanoyl for example acetyl; $C_{1-6}$alkanoyloxy for example acetoxy; $C_{1-6}$alkyl for example methyl, ethyl, isopropyl or tert-butyl; halo for example fluoro, chloro or bromo; trifluoromethyl or trifluoromethoxy. In another aspect a further typical substituent for any phenyl group is phenyl$C_{1-6}$alkoxy.

In one aspect the present invention provides a compound of the formula (I) or a pharmaceutically acceptable salt or in vivo hydrolysable amide or carbamate thereof, wherein
R is hydrogen, $C_{1-6}$alkyl, $C_{3-8}$cycloalkyl, $C_{3-8}$cycloalkyl$C_{1-6}$alkyl, phenyl$C_{1-6}$alkyl or phenyl;
$R^1$ is
$C_{1-6}$alkyl, $C_{1-6}$alkoxy, halo, hydroxy, halo$C_{1-6}$alkyl, cyano or nitro; m is 0, 1 or 2; $R^2$ $C_{1-6}$alkyl; and n is 0, 1 or 2; wherein any phenyl ring is optionally substituted.

Suitably R is hydrogen; $C_{1-10}$alkyl for example methyl, ethyl, n-propyl, isopropyl, n-butyl, isobutyl, pentyl (n-pentyl or 3-methylbutyl) or 2-ethylheptyl; $C_{3-8}$cycloalkyl for example cyclopropyl, cyclobutyl or cyclopentyl; $C_{3-8}$cycloalkyl$C_{1-6}$alkyl for example cyclopropylmethyl, cyclobutylmethyl or cyclopentylmethyl; phenyl$C_{1-6}$alkyl for example benzyl, 2-phenethyl or 3-phenylpropyl.

Favourably R is hydrogen or $C_{1-6}$alkyl. In particular R is hydrogen or $C_{1-4}$alkyl such as methyl, ethyl, isopropyl, n-propyl, n-butyl or isobutyl. In particular also R is $C_{5-6}$alkyl for example 3-methylbutyl. Another particular value for R is phenyl$C_{1-6}$alkyl for example benzyl, 2-phenethyl or 3-phenylpropyl. In one aspect R is $C_{1-6}$alkyl or phenyl$C_{1-6}$alkyl. Preferably R is methyl, 3-methylbutyl or 3-phenylpropyl. In one aspect R is $C_{1-6}$alkyl or phenyl$C_{1-6}$alkyl.

Suitably $R^1$ is $C_{1-6}$alkyl for example methyl, ethyl or propyl; $C_{2-6}$alkenyl for example vinyl; $C_{1-6}$alkoxy for example methoxy, ethoxy or propoxy; halo for example bromo, chloro or fluoro; hydroxy; $C_{1-6}$alkanoyl for example formyl or acetyl; halo$C_{1-6}$alkyl for example trifluoromethyl; cyano or nitro In one aspect $R^1$ is $C_{1-6}$alkyl, $C_{1-6}$alkoxy, halo, hydroxy, halo$C_{1-6}$alkyl, cyano or nitro.

Preferably $R^1$ is $C_{1-6}$alkoxy for example methoxy or ethoxy or is halo for example bromo chloro or fluoro. In a particularly preferred aspect, m is one and $R^1$ is methoxy, for example at the 5-position or the 7-position of the 1,2,3,4-tetrahydronaphthalene ring system, most preferably at the 5-position. In another particularly preferred aspect, m is one and $R^1$ is bromo or fluoro, for example at the 6-position of the 1,2,3,4-tetrahydronaphthalene ring system.

In another preferred aspect m is zero.

Suitably $R^2$ is $C_{1-6}$alkyl for example methyl or ethyl.

In a preferred aspect n is zero.

A particular class of preferred compounds is that of the formula (II):

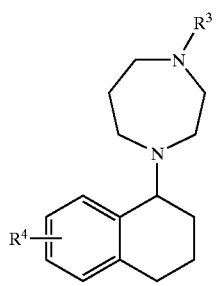

(II)

wherein $R^3$ is hydrogen, or $C_{1-6}$alkyl or pheny $C_{1-6}$alkyl and $R^4$ is hydrogen or $C_{1-6}$alkoxy. In one aspect $R^3$ is $C_{1-6}$alkyl. In particular in the compounds of the formula (II), $R^4$ is hydrogen and $R^3$ is methyl, 3-methylbutyl or 3-phenylpropyl.

Particular compounds of the present invention include those of the Examples hereinafter; 4-(7-methoxy-1,2,3,4-tetrahydro-1-naphthalenyl)homopiperazine 1-methyl-4-(7-methoxy-1,2,3,4-tetrahydro-1-naphthalenyl)homopiperazine and 1-isopropyl-4-(5-methoxy-1,2,3,4-tetrahydro-1-naphthalenyl)homopiperazine The compounds of the present invention possess a chiral centre at the 1-position of the 1,2,3,4-tetrahydronaphthalene ring system (that is the carbon atom to which the nitrogen containing ring is attached). Other chiral centres may be present when n is one or two and in any of the substituents R–$R^4$.

The present invention covers all enantiomers, diastereoisomers and mixtures thereof of the compound of the formula (I) that inhibit the [3H]-emopamil binding site.

As mentioned hereinabove, the compounds of the present invention possess a chiral centre at the 1-position of the 1,2,3,4-tetrahydronaphthalene ring system. It is preferred that this centre has the S-stereochemistry under the Cahn-Prelog-Ingold sequence rules. It is preferred that any R or S-enantiomer is substantially free of the corresponding S or R-enantiomer, suitably 90%, more suitably 95%, and for example 96%, 97%, 98% or 99% free of the other enantiomer.

Suitable pharmaceutically acceptable salts include acid addition salts such as hydrochloride, hydrobromide, citrate and maleate salts and salts formed with phosphoric and sulphuric acid. In another aspect suitable salts are base salts such as an alkali metal salt for example sodium or potassium, an alkaline earth metal salt for example calcium or magnesium, or organic amine salt for example triethylamine.

In vivo hydrolysable esters, amides and carbamates hydrolyse in the human body to produce the parent compound. Such esters, amides and carbamates can be identified by administering, for example intravenously to a test animal, the compound under test and subsequently examining the test animal's body fluids. Suitable in vivo hydrolysable groups include N-carbomethoxy and N-acetyl.

In order to use a compound of the formula (I) or a pharmaceutically acceptable salt or in vivo hydrolysable ester amide or carbamate thereof for the therapeutic treatment (including prophylactic treatment) of mammals including humans, it is normally formulated in accordance with standard pharmaceutical practice as a pharmaceutical composition.

Therefore in another aspect the present invention provides a pharmaceutical composition which comprises a compound of the formula (I) or a pharmaceutically acceptable salt or an in vivo hydrolysable ester amide or carbamate and a pharmaceutically acceptable carrier.

The pharmaceutical compositions of this invention may be administered in standard manner for the disease condition that it is desired to treat, for example by oral, topical, parenteral, buccal, nasal, vaginal or rectal administration or by inhalation. For these purposes the compounds of this invention may be formulated by means known in the art into the form of, for example, tablets, capsules, aqueous or oily solutions, suspensions, emulsions, creams, ointments, gels, nasal sprays, suppositories, finely divided powders or aerosols for inhalation, and for parenteral use (including intravenous, intramuscular or infusion) sterile aqueous or oily solutions or suspensions or sterile emulsions. A preferred route of administration is intravenously in sterile isotonic solution.

In addition to the compounds of the present invention the pharmaceutical composition of this invention may also contain, or be co-administered (simultaneously or sequentially) with, one or more pharmacological agents of value in treating one or more disease conditions referred to hereinabove.

The pharmaceutical compositions of this invention will normally be administered to humans so that, for example, a daily dose of 0.05 to 75 mg/kg body weight (and preferably of 0.1 to 30 mg/kg body weight) is received. This daily dose may be given in divided doses as necessary, the precise amount of the compound received and the route of administration depending on the weight, age and sex of the patient being treated and on the particular disease condition being treated according to principles known in the art.

Typically unit dosage forms will contain about 1 mg to 500 mg of a compound of this invention.

Therefore in a further aspect, the present invention provides a compound of the formula (I) or a pharmaceutically acceptable salt or an in vivo hydrolysable ester, amide or carbamate thereof for use in a method of therapeutic treatment of the human or animal body.

In yet a further aspect the present invention provides a method of treating a disease condition wherein inhibition of the [3H]-emopamil binding site is beneficial which comprises administering to a warm-blooded animal an effective amount of a compound of the formula (I) or a pharmaceutically acceptable salt or an in vivo hydrolysable ester, amide or carbamate thereof. The present invention also provides the use of a compound of the formula (I) or a pharmaceutically acceptable salt or an in vivo hydrolysable ester, amide or carbamate thereof in the preparation of a medicament for use in a disease condition.

In another aspect the present invention provides a process for preparing a compound of the formula (I) or a pharmaceutically acceptable salt or an in vivo hydrolysable ester, amide or carbamate thereof which process comprises:

a) reacting a compound of the formula (III) with a compound of the formula (IV):

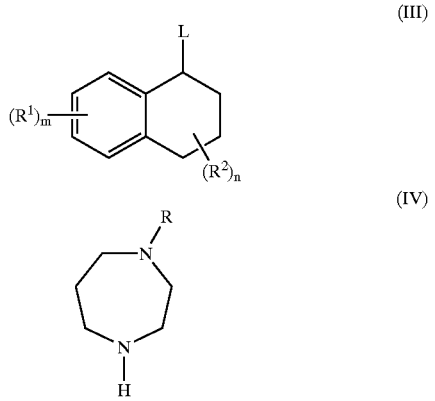

(III)

(IV)

wherein R, $R^1$, $R^2$, m and n are as hereinbefore defined and L is a leaving group; or b) deprotecting a compound of the formula (V):

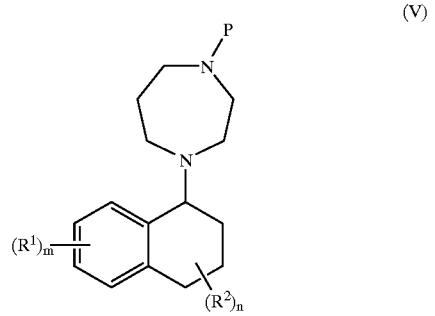

(V)

wherein $R^1$, $R^2$, m and n are as hereinbefore defined and P is a protecting group for R;
wherein any functional group is protected, if necessary, and:
  i) removing any protecting groups;
  ii) optionally converting a compound of the formula (I) into another compound of the formula (I);
  iii) optionally forming a pharmaceutically acceptable salt or an in vivo hydrolysable ester, amide or carbamate.

Protecting groups may in general be chosen from any of the groups described in the literature or known to the skilled; chemist as appropriate for the protection of the group in question, and may be introduced by conventional methods.

Protecting groups may be removed by any convenient method as described in the literature or known to the skilled chemist as appropriate for the removal of the protecting group in question such methods being chosen so as to effect removal of the protecting group with minimum disturbance of groups elsewhere in the molecule.

Specific examples of protecting groups are given below for the sake of convenience, in which "lower" signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxyl protecting group may be the residue of an ester-forming aliphatic or araliphatic alcohol or of an ester-forming silanol (the said alcohol or silanol preferably containing 1–20 carbon atoms).

Examples of carboxy protecting groups include straight or branched chain (1–12C)alkyl groups (eg isopropyl, t-butyl); lower alkoxy lower alkyl groups (eg methoxymethyl, ethoxymethyl, isobutoxymethyl); lower aliphatic acyloxy lower alkyl groups, (eg acetoxymethyl, propionyloxymethyl, butyryloxymethyl, pivaloyloxymethyl); lower alkoxycarbonyloxy lower alkyl groups (eg 1-methoxycarbonyloxyethyl, 1-ethoxycarbonyloxyethyl); aryl lower alkyl groups (eg benzyl, p-methoxybenzyl, o-nitrobenzyl, p-nitrobenzyl, benzhydryl and phthalidyl); tri(lower alkyl)silyl groups (eg trimethylsilyl and t-butyldimethylsilyl); tri(lower alkyl)silyl lower alkyl groups (eg trimethylsilylethyl); and (2–6C) alkenyl groups (eg allyl and vinylethyl).

Methods particularly appropriate for the removal of carboxyl protecting groups include for example acid-, base-, metal- or enzymically-catalysed hydrolysis.

Examples of hydroxyl protecting groups include lower alkyl groups (eg t-butyl), lower alkenyl groups (eg allyl); lower alkanoyl groups (eg acetyl); lower alkoxycarbonyl groups (eg t-butoxycarbonyl); lower alkenyloxycarbonyl groups (eg allyloxycarbonyl); aryl lower alkoxycarbonyl groups (eg benzoyloxycarbonyl, p-methoxybenzyloxycarbonyl, o-nitrobenzyloxycarbonyl, p-nitrobenzyloxycarbonyl); tri(lower alkyl)silyl (eg trimethylsilyl, t-butyldimethylsilyl) and aryl lower alkyl (eg benzyl) groups.

Examples of amino protecting groups include formyl, aralkyl groups (eg benzyl and substituted benzyl, p-methoxybenzyl, nitrobenzyl and 2,4-dimethoxybenzyl, and triphenylmethyl); di-p-anisylmethyyl and furylmethyl groups; lower alkoxycarbonyl (eg t-butoxycarbonyl); lower alkenyloxycarbonyl (eg allyloxycarbonyl); aryl lower alkoxycarbonyl groups (eg benzyloxycarbonyl, p-methoxybenzyloxycarbonyl, o-nitrobenzyloxycarbonyl, p-nitrobenzyloxycarbonyl); trialkylsilyl (eg trimethylsilyl and t-butyldimethylsilyl); alkylidene (eg methylidene); benzylidene and substituted benzylidene groups.

Methods appropriate for removal of hydroxy and amino protecting groups include, for example, acid-, base-, metal- or enzymically-catalysed hydrolysis, for groups such as p-nitrobenzyloxycarbonyl, hydrogenation and for groups such as o-nitrobenzyloxycarbonyl, photolytically.

Pharmaceutically acceptable salts of the compound of the formula (I) may be prepared in any conventional manner for example from the free base and acid. In vivo hydrolysable esters, amides and carbamates may be prepared in any conventional manner.

The reaction between the compounds of the formulae (III) and (IV) is performed in conventional manner. Typically this reaction takes place in organic solvent for example an anhydrous aprotic solvent such as dimethylformamide, dimethylacetamide or tetrahydrofuran. The reaction is generally performed in the presence of a catalyst, such as an iodide salt for example potassium iodide, and is generally performed at ambient. or elevated temperature for example 0°–100° C., more preferably 40°–80° C.

In the compounds of the formula (III), L is a conventional leaving group such as halo for example chloro, iodo or bromo; or a tosylate for example p-toluenesulphonyloxy or methanesulphonyloxy.

In the compounds of the formula (III), the leaving group L may also represent oxo (=O), forming an a-tetralone ring system. Such compounds may be reacted with a compound of the formula (IV) under conventional conditions for reductive amination. Suitable conditions include the presence of a reducing agent such as hydrogen and a hydrogenation catalyst (for example palladium on carbon), or zinc and hydrochloric acid, or sodium cyanoborohydride, or sodium triacetoxyborohydride, or sodium borohydride, iron pentacarbonyl and alcoholic potassium hydroxide, or borane and pyridine or formic acid. The reaction is preferably carried out in the presence of a suitable solvent such as an alcohol, for example methanol or ethanol, and at a temperature in the range of 0–50° C., preferably at or near room temperature.

The compounds of the formula (III) are either known or may be prepared in conventional manner as known to the organic chemist skilled in the art. One convenient manner is to convert the corresponding 1-hydroxy-1,2,3,4-tetrahydronaphthalene to the compound of the formula (III); for example by treating with thionyl chloride in the presence of pyridine to prepare the compound of the formula (III) wherein L is chloro.

Compounds of the formula (V) wherein P is a protecting group convertible to R may be deprotected in standard manner. Any suitable N-protecting group may be used and deprotected in conventional manner. Favourably P is $C_{1-6}$alkoxycarbonyl and such compounds may be converted to compounds of the formula (I) wherein R is methyl for example by treating with a reducing agent such as lithium aluminium hydride. Certain compounds of the formula (V) are also in vivo hydrolysable esters, amides or carbamates of the compounds of the formula (I).

Compounds of the formula (I) wherein R is hydrogen may be converted to compounds of the formula (I) wherein R is other than hydrogen. For example such conversion may comprise conventional methods of alkylation with an appropriate alkylating agent or reductive amination. For example an isopropyl group may be prepared by reacting a compound of the formula (I) wherein R is hydrogen with acetone in the presence of a reducing agent such as sodium borohydride or sodium cyanoborohydride. A 2-methylpropyl group may be prepared by reacting a compound of the formula (I) wherein R is hydrogen with isobutyric acid in the presence of a reducing agent such as sodium borohydride or sodium cyanoborohydride.

Thus in another aspect the present invention provides a process for preparing a compound of the formula (I) wherein R is not hydrogen, especially where R is $C_{1-10}$alkyl, from a compound of the formula (I) wherein R is hydrogen by reaction with an alkylating agent or by reductive amination.

As mentioned hereinabove, the compounds of the present invention possess a chiral centre at the 1-position of the 1,2,3,4-tetrahydronaphthalene ring system and the present invention encompasses the racemate and individual enantiomers. Enantiomers of the compound of the formula (I) may be prepared in conventional manner by resolution of a racemic compound. Alternatively enantiomers of the compounds of the formula (I) may be prepared in analogous manner to the racemates commencing with chiral starting-materials. In yet a further alternative, a chemical intermediate, for example of the formula (III), or the corresponding hydroxy compound, or of the formula (V), may be resolved and subsequently reacted without destroying chirality.

The following biological test methods, data and Examples serve to illustrate the present invention.

$^3$H-Emopamil Binding to Guinea Pig Liver Membranes

The method of (−)-$^3$H-emopamil binding was a modification of Zech, C., Staudinger R., Mühlbacher, J. and Glossmann, H. Novel sites for phenylalkylamines: characterization of a sodium-sensitive drug receptor with (−)-$^3$H-emopamil. Eur. J. Pharm. 208: 119–130, 1991.

The reaction mixture contained:

Assay buffer: 10 mM Tris-HCl, 0.1 mM phenylmethylsulfonyl fluoride (PMSF), 0.2% bovine serum albumin (BSA), pH 7.4 at 4° C.

Radioligand: 0.96 nM (−)-$^3$H-emopamil (Amersham).

Guinea pig liver membranes: 40 mg/mL original wet weight.

Compounds: 1–300 nM.

Total volume: 500 μL.

This mixture was incubated for 60 minutes at 37° C. The incubation was terminated by filtering with a Brandel Cell Harvester over Whatman GF/C filters that had been soaked for at least 120 minutes in 0.3% polyethylenimine (PEI) and washed three times with 5 mL of wash buffer containing 10 mM Tris-HCl, 10 mM $MgCl_2$, 0.2% BSA, pH 7.4 at 25° C. Specific binding was defined with 10 μM emopamil. In general compounds with an $IC_{50}$ Specific binding was defined with 10 μM emopamil. In general compounds with an $IC_{50}$ below 300 nM in this test were of interest and for example the compound of Example 4 gave a value of 17 nM.

Guinea-pig liver membrane preparation: Male guinea pigs were sacrificed by $CO_2$ asphyxiation with dry ice. The livers were quickly excised and weighed and rinsed in membrane preparation buffer containing 10 mM Hepes, 1 mM Tris base-EDTA, 250 mM driven Teflon-glass homogenizer with three strokes on ice. The homogenate was centrifuged driven Teflon-glass homogenizer with three strokes on ice. The homogenate was centrifuged at 1000×g in a SS34 rotor for 5 minutes at 4° C. The supernatant was filtered through 4 layers of gauze and then centrifuged at 8000×g for 10 minutes at 4° C. This resulting supernatant was centrifuged at 40,000×g for 15 minutes at 4° C. The resulting pellet was resuspended in assay buffer and centrifuged again at 40,000×g for 15 minutes at 4° C. This pellet was resuspended in assay buffer (2.5 fold with respect to original wet weight) and homogenized with one stroke with the Teflon-glass homogenizer. Aliquots of 1 mL were stored at −70° C.

$^3$H-D-888 Binding to Rat Brain Cortical Membranes

The method of $^3$H-D-888 binding was a modification of Reynolds, I. J., Snowman, A. M. and Synder, S. H. (−)-[$^3$H] Desmethoxyverapamil labels multiple calcium channel modular receptors in brain and skeletal muscle membranes: differentiation by temperature and dihydropyridines. J. Pharmacol. Exp. Ther. 237: no.3, 731–738, 1986.

The assay tubes contained the following:

assay buffer: 50 mM Hepes, 0.2% BSA, pH 7.4 radioligand: 1 πM $^3$H-D888 (Amersham)

rat cortical membranes: 6 mg/ml original wet weight compounds: 0.3–100 μM

Total volume: 1000 μL

This mixture was incubated for 60 minutes at 25° C. The assay was terminated by filtering with a Brandel Cell Harvester over Whatman GF/C filters that had been soaked for at least 120 minutes in 0.3% polyethylenamine (PEI) and washed three times with 5 mL of wash buffer containing 20 mM Hepes, 20 mM $MgCl_2$, pH 7.4. Specific binding was measured with 10 µM methoxyverapamil (D-600). This assay was used to determine in vitro selectivity of compounds vs. L-type voltage sensitive calcium channels, i.e high affinity for the $^3$H-D888 binding site would show a lack of selectivity. For example the compound of Example 4 gave a value of about 19.000 nM in this test.

Rat brain cortical membrane preparation: Male Sprague-Dawley Rats were sacrificed by decapitation and the brains were quickly excised. The cerebellum and brain stem were removed and discarded; and the rest of the brain was rinsed in 320 mM sucrose. The brain was then homogenized in a 10-fold volume of 320mM sucrose with a motor driven Teflon-glass homogenizer using 10 strokes on ice. The homogenate was spun at 1000×g for 10 glass homogenizer using 10 strokes on ice. The homogenate was spun at 1000×g for 10 minutes at 4° C. in a SS-34 rotor. The supernatant was then spun at 29,000×g for 20 minutes. The resulting pellet was resuspended in membrane buffer (5 mM Hepes, 0.2% BSA, pH 7.4 ) to a final concentration of 60 mg original wet weight/mL.

Gerbil Global Model of Cerebral Ischemia

Male Mongolian gerbils (Charles River) weighing 60–70 grams are used in these experiments. They are housed in individual cages with food (Purina Rodent Chow) and water available ad libitum. The animal room is maintained at 23° C.±2°, and is on an automatic 12 hour light cycle.

The gerbils are brought to the surgical suite and dosed intraperitoneally with the test agent or vehicle, forty five minutes prior to surgery. Drugs are administered at a volume of 5 ml/kg (intraperitoneal). Vehicle is generally saline, with sodium phosphate added to adjust pH, if needed. Forty-five minutes after dosing the gerbils are anesthetized with halothane (3.3%) which is delivered along with oxygen (1.5 L/M) through a face mask. After the gerbils are anesthetized, halothane is continued at a maintenance level of 1.5–2% along with oxygen. The ventral surface of the neck is shaved and cleaned with alcohol. Surgical procedures are carried out on a thermostat-controlled heating pad set to 37° C. An incision is made in the neck, the carotid arteries are dissected away from the surrounding tissue, and isolated with a 5 cm length of Silastic tubing. When both arteries have been isolated they are clamped with microaneurysm clips (Roboz Instruments). The arteries are visually inspected to determine that the blood flow has been stopped. After 5 minutes the clips are gently removed from the arteries and blood flow begins again. A sham control group is treated identically but is not subjected to carotid artery occlusion. The incisions are closed with suture and the gerbils removed from the anesthesia masks and placed on another heating pad to recover from the anesthesia. When they have regained the righting reflex and are beginning to walk around, they are again dosed with the test compound and returned to their home cages. This occurs approximately five minutes after the end of surgery.

Twenty-four hours post ischemia gerbils are tested for spontaneous locomotor activity, using a Photobeam Activity System from San Diego Instruments. They are individually placed in Plexiglas chambers measuring 27.5 cm×27.5 cm×15 cm deep. The chambers are surrounded by photocells, and every time a beam is broken one count is recorded. Each gerbil is tested for two hours, and cumulative counts are recorded at 30, 60, 90, and 120 minutes. Mean counts are recorded for each group and drug groups are compared to control with an ANOVA and Bonferroni post test. After each gerbil is tested it is returned to its home cage. At this time gerbils are also observed for any changes from normal behavior.

For the next two days no specific testing is performed, but the gerbils are observed two to three times per day for any unusual behaviors or obvious neurological symptoms (i.e. ataxia, convulsions, stereotypic behavior). Four days post ischemia the gerbils are sacrificed by decapitation and their brains removed and preserved in 10% buffered formalin. Brains were removed, fixed and stained with hematoxylin and eosin. Under a light microscope, hippocampal fields were observed and graded for damage to the CA1 subfield: 0 to 4 scale, with 0 representing no damage and 4 representing extensive damage.

Transient Focal Ischemia in Rats

The method was as described by Lin, T-N., He, Y. Y., Wu, G., Khan, M. And Hsu, C. Y. Effect of brain edema on infarct volume in a focal model cerebral ischemia model in rats. Stroke 24:117–121, 1993, which model is considered to be relevant to the clinical situation. Male Long-Evans rats 250–350 g were used. Surgery leading to focal ischemia was conducted under anesthesia with 100 mg/kg ketamine and 5 mg/kg i.m. xylazine. Rectal temperature was monitored and maintained at 37.0±0.5 deg C. The right middle cerebral artery (MCA) was exposed using microsurgical techniques. The MCA trunk was ligated immediately above the rhinal fissure with 10-0 suture. Complete interruption of blood flow was confirmed under an operating microscope. Both common carotid arteries were then occluded using nontraumatic aneurysm clips. After a predetermined duration of ischemia (45 min), blood flow was restored in all three arteries. Twenty-four hours post occlusion, rats were killed under ketamine anesthesia by intracardiac perfusion with 200 ml of 0.9% NaCl. The brain was removed and processed with 2% triphenyltetrazolium chloride to identify and quantitate the infarcted brain region. Compounds were administered by intravenous infusion for 4 hours.

In the examples:
a) all nmr spectra were recorded at 300 MHz and were recorded in $CDCl_3$ unless otherwise stated;
b) evaporation of solvents was carried out under reduced pressure;
c) DMF means N,N-dimethylformamide;
d) DMAC means N,N-dimethylacetamide;
e) THF means tetrahydrofuran.

EXAMPLE 1

1-Methyl-4-(1,2,3,4-tetrahydro-1-naphthalenyl) homopiperazine

A 1 liter 3-necked flask equipped with a condenser, electronic thermocouple, mechanical stirrer and under a nitrogen atmosphere was charged with a solution of N-methylhomopiperazine (60 ml; 0.476 mol) in DMF (200 ml). Potassium iodide (8.7 g) was added followed by the addition in one portion of a solution of 1,2,3,4-tetrahydro-1-chloronaphthalene (36.8 g: 0.22 mol) in DMF (150 ml). This solution was then heated at 68° C. for 18 hours and the solvent was removed in vacuo using a rotary evaporator. The resulting concentrate was diluted with water (800 ml) and extracted with ethyl acetate (3×300 ml) which was washed with brine and dried with sodium sulphate. Filtration and evaporation of solvent gave a brown oil (47.3 g) which was purified by flash chromatography using 2000 ml of silica gel and eluting with methylene chloride:methanol:ammonium hydroxide in gradients of 94:5:1, 89:10:1 and 79:20:1. The resulting tan oil (46.5 g) was distilled using a Kugelrohr to give the title compound as a yellow oil (38.8 g); bp (air bath temperature) 123–138° C. at 650–950 mtorr; $^1$H nmr δ 3.86–3.91(m, 1H), 7.03–7.78 (m, 3H), 7.76–7.78 (d, 1H).

A solution of the above base (38.8 g) in ethanol (800 ml) was treated with saturated ethanolic HCl (400 ml). While stirring, diethyl ether (1200 ml) was added over 10 minutes, resulting in the separation of a white solid after 15 minutes. After 2 hours this solid was collected by filtration and dried at 70° C. in vacuo to yield the dihydrochloride of the title compound (44.6 g) mp 221–222° C. Anal; Calcd. for $C_{16}H_{24}N_2 \cdot 2HCl \cdot 0.3\ H_2O$: C, 59.55; H, 8.31; N, 8.68. Found: C, 59.40; H, 8.28; N. 8.40.

A solution of the base (1.46 g) in ethanol (31 ml) was treated with an ethereal solution (62 ml) saturated with maleic acid (prepared by dissolving 1.94 gm of maleic acid in 70 ml of diethyl ether) and left at ambient temperature overnight. The resulting white solid was collected by filtration and dried in vacuo at 57° C. to give the dimaleate salt of the title compound (2.61 g) mp 125.4–126.3° C. Anal; Calcd. for $C_{16}H_{24}N_2 \cdot 2C_4H_4O_4$: C, 60.49; H, 6.77; N, 5.88. Found: C, 60.48; H, 6.64; N, 5.96. 1,2,3,4-Tetrahydro-1-chloronaphthalene was prepared as follows:

A 1 liter 3-necked flask equipped with a condenser, electronic thermocouple, mechanical stirrer and under a nitrogen atmosphere was charged with 1,2,3,4-tetrahydro-1-naphthol (34.3 g; 0.23 mol) in dry diethyl ether (420 ml). Pyridine (4.7 ml) was added and the flask was cooled to 16° C. in a bath of water and ice. A solution of thionyl chloride (50.7 ml; 0.70 mol) in ether (140 ml) was then added dropwise in 25 minutes and stirring continued overnight while allowing the bath to warm to ambient temperature. The reaction mixture was then poured into cold brine (400 g ice and 800 ml brine) and the organic phase was separated. The aqueous phase was extracted with diethyl ether (2×150 ml) and the combined organic extract was dried with sodium sulphate. Filtration and removal of solvent in vacuo gave 1,2,3,4-tetrahydro-1-chloronaphthalene (36.9 g) as an oil. This material was used without further purification.

EXAMPLE 2

N-(1,2,3,4-Tetrahydro-1-naphthalenyl) homopiperazine

A 250 ml 3-necked flask equipped with a condenser and magnetic stirring bar and under a nitrogen atmosphere was charged with a solution of homopiperazine (19.2 g; 186 mmol) in DMF (90 ml). Potassium iodide (100 mg) was added followed by the addition by pipette of a solution of 1,2,3,4-tetrahydro-1-chloronaphthalene (6.35 g; 38.1 mmol) in DMF (20 ml). This solution was then heated in an oil bath at 55° C. for 43 hours. The reaction mixture was partitioned between water and ethyl acetate, washed with brine and dried with magnesium sulphate. Filtration and evaporation of solvent gave an amber liquid (7.5 g) which was purified by Kugelrohr distillation to give the title compound as a pale yellow oil (5.3 g) bp (air bath temperature) 120–140° C. at 90 mtorr; tlc analysis on silica gel ($CH_2Cl_2$:$CH_3OH$:$NH_4OH$, 89:10:1) showed a single component, $R_f$ 0.11; $^1$H nmr δ 3.90–3.95 (m, 1H, benzylic CHN), 7.03–7.37 (m, 3H), 7.77–7.80 (d, 1H).

An ethanolic solution (21 ml) containing this base (1.00 g) was treated dropwise with an ethereal solution (43 ml) saturated with maleic acid to the cloud point. A gum which formed on standing very slowly solidified. This white solid was collected by filtration, washed with ether and dried at 60° C. at high vacuum to yield the salt of the title compound (0.95 g) mp 107–109.4° C.; $^1$H nmr (300 MHz, $d_6$-DMSO) δ 3.96 (m, 1H, benzylic CHN), 6.11 (3.44H, CH=CH, maleic acid), 7.05–7.18 (m, 3H), 7.72 (d, 1H). Anal. Calcd. for $C_{15}H_{22}N_2 \cdot 1.70 C_4H_4O_4$: C, 61.22; H, 6.79; N, 6.55. Found: C, 61.06; H, 6.91; N, 6.73.

EXAMPLE 3

S(+) N-(1,2,3,4-Tetrahydro-1-naphthalenyl) homopiperazine

S(+) N-(1,2,3,4-tetrahydro-1-naphthalenyl) homopiperazine was obtained as the first material to elute on subjecting racemic material (5.3 g), prepared as in Example 2, to preparative Chiral Pak AD HPLC resolution using a hexane/ethanol mixture with modification with diethylamine. The enantiomeric purity was determined on an analytical scale using hexane:ethanol:diethylamine (90:5:.05, v/v) and detection at 220 nm. The solution containing this enantiomer was concentrated using a rotary evaporator to give the title compound (2.35 g), $[\alpha]_D^{22}+108°$ (c=0.50, methanol); 98% ee.

To a solution of this base (1.0 g; 4.35 mmol), in ethanol (25 ml) was added by pipette a solution of maleic acid (1.1 g; 9.47 mmol) in ether (40 ml). Addition of ether (5 ml) resulted in a cloudiness and, on standing, the formation of a white precipitate. This solid was collected by filtration and dried in a drying pistol (50° C., 70 mtorr) to yield the dimaleate of the title compound (0.76 g), mp 106–107.5° C.; $[\alpha]_D^{22}+44.7°$ (c=0.38, methanol). Anal: Calcd. for $C_{15}H_{22}N_2 \cdot 2C_4H_4O_4$: C, 59.73; H, 6.53; N, 6.05. Found: C, 59.83; H, 6.62; N, 6.00.

EXAMPLE 4

S(+) 1-Methyl-4-(1,2,3,4-tetrahydro-1-naphthalenyl) homopiperazine

A dry 100 ml 3-necked flask equipped with a condenser, addition funnel and magnetic stirring bar was charged with lithium aluminum hydride (0.36 g; 9.48 mmol) and dry THF (10 ml) under a nitrogen atmosphere. S(+) N-Carbethoxy-N'-(1,2,3,4-tetrahydro-1-naphthalenyl)homopiperazine (1.35 g: 4.47 mmol) in THF (10 ml) was added dropwise and the solution was heated to reflux for 3 hours and cooled to ambient temperature. Saturated sodium sulphate (10 ml) was added dropwise at a rate amenable to maintaining control of the reaction and the content of the flask was filtered through diatomaceous earth and dried ($MgSO_4$). Filtration and removal of solvent in vacuo gave a yellow oil (1.06 g) which was kugelrohr distilled to give the title compound (0.97 g) bp (air bath temperature) 150° C. at 100 mtorr., homogeneous by tlc (silica gel, $CH_3OH$:$CH_2Cl_2$:$NH_4OH$ 10:89:1), $R_f$ 0.40; $^1$H-nmr δ 3.88–3.91 (m, 1H, benzylic CHN), 6.97–7.25 (m, 3H), 7.75–7.78 (d, 1H); $[\alpha]_D^{22}+85.2°$ (c=0.54, methanol).

To a solution of the base (0.91 g) in ethanol (25 ml) was added by pipette a solution of maleic acid (1.0 g) in ether (40 ml). Upon completion of the addition, a white precipitate formed. This solid was collected by filtration and was dried overnight in a drying pistol (50° C. at 100 mtorr) to yield the dimaleate salt of the title compound (1.40 g) mp 135.1–135.3; $^1$H-nmr (300 MHz, $d_6$-DMSO) δ 3.95–3.98 (m, 1H, benzylic, CHN), 6.11 (s, CH=CH, maleic acid), 7.05=7.71 (m, 3H), 7.69–7.71 (d, 1H): $[\alpha]_D^{22}$+41° (c=0.245, methanol). Anal: Calcd. for $C_{16}H_{24}N_2.2C_4H_4O_4$: C, 6049; H, 6.77; N, 5.88. Found: C, 60.20; H, 6.74; N, 5.99.

S(+) N-Carbethoxy-N'-(1,2,3,4-tetrahydro-1-naphthalenyl)homopiperazine was obtained as follows:

A dry 50 ml 3-necked flask equipped with a condenser, addition funnel and magnetic stirring bar under a nitrogen atmosphere was charged with S(+) N-(1,2,3,4-tetrahydro-1-naphthalenyl)homopiperazine (1.0 g; 4.34 mmol) and methylene chloride (15 ml). Triethylamine (0.80 ml; 5.74 mmol) was added and the flask was cooled in a Dry Ice/acetone bath. Ethyl chloroformate (0.50 ml; 5.23 mmol), in methylene chloride (10 ml) was added dropwise and the mixture was allowed to warm to ambient temperature slowly. After stirring overnight, the content of the flask was partitioned between water and methylene chloride, the organic phase was washed with brine and the solution was dried with magnesium sulphate. Filtration and removal of solvent gave an amber oil (1.30 g), homogeneous by tlc (silica gel, ethyl acetate), $R_f$ 0.68; $^1$H-nmr δ 1.24–1.28 (t, 3H), 4.11–4.18 (q, 2H), 7.03–7.26 (m, 3H), 7.74(1H).

EXAMPLE 5

R(-) N-(1,2,3,4-Tetrahydro-1-naphthalenyl)homopiperazine

R(-) N-(1,2,3,4-tetrahydro-1-naphthalenyl)homopiperazine was obtained as the second material to elute on subjecting racemic material (5.3 g), prepared as in Example 2, to preparative Chiral Pak AD HPLC resolution using a hexane/ethanol mixture with modification with diethylamine. The enantiomeric purity was determined on an analytical scale using hexane:ethanol:diethylamine (90:5:.05, v/v) and detection at 220 nm. The solution containing this enantiomer was concentrated using a rotary evaporator to give the title compound (2.65 g), $[\alpha]_D^{22}$–94° (c=0.64, methanol); 98.5% ee.

To a solution of this base (1.1 g: 4.78 mmol) in ethanol (25 ml) was added by pipette a solution of maleic acid (1.2 g; 10.33 mmol) in ether (40 ml) and the formation of a white solid was promoted by scratching. This solid was collected by filtration and dried in a drying pistol (50° C., 70 mtorr) to yield the dimaleate salt of the title compound (1.2 g), mp 108–110° C.; $[\alpha]_D^{22}$–41.6° (c=0.60, methanol). Anal. Calcd. for $C_{15}H_{22}N_2.2C_4H_4O_4$: N, 6.05. Found: C, 59.62; H, 6.56; N, 6.09.

EXAMPLE 6

R(-) 1-Methyl-4-(1,2,3,4-tetrahydro-1-naphthalenyl)homopiperazine

A dry 50 ml 3-necked flask equipped with a condenser, addition funnel and magnetic stirring bar was charged with lithium aluminum hydride (0.37 g, 9.75 mmol) and dry THF (10 ml) under a nitrogen atmosphere. R(-) N-Carbethoxy-N'-(1,2,3,4-tetrahydro-1-naphthalenyl)homopiperazine (1.45 g; 4.80 mmol) in THF (10 ml) was added dropwise and the solution was heated to reflux for 3 hours and cooled to ambient temperature. Saturated sodium sulphate (10 ml) was added dropwise at a rate amenable to maintaining control of the reaction and the content of the flask was filtered through diatomaceous earth and dried ($MgSO_4$). Filtration and removal of solvent in vacuo gave a yellow oil (1.06 g) which was kugelrohr distilled to give the title compound (0.97 g), bp (air bath temperature) 120–130° C. at 70 mtorr., homogeneous by tlc (silica gel, $CH_3OH:CH_2Cl_2:NH_4OH$ 10:89:1), $R_f$ 0.40; $^1$H-nmr δ 3.87–3.91 (m, 1H, benzylic CHN), 6.98–7.26 (m, 3H), 7.76–7.78 (d, 1H); $[\alpha]_D^{22}$–86.5° (c=0.70, methanol).

To a solution of the base (0.95 g) in ethanol (25 ml) was added by pipette a solution of maleic acid (1.0 g) in ether (40 ml). Upon completion of the addition, a white precipitate formed. This solid was collected by filtration and was dried overnight in a drying pistol (50° C. at 100 mtorr) to yield the dimaleate salt of the title compound (1.59 g), mp 138–139; $^1$H-nmr (300 MHz, $d_6$-DMSO) δ 3.95–3.98 (m, 1H, benzylic, CHN), 6.11 (s, CH=CH, maleic acid), 7.05=7.71 (m, 3H), 7.69–7.71 (d, 1H). Anal: Calcd. for $C_{16}H_{24}N_2.2C_4H_4O_4$: C, 60.49; H, 6.77; N, 5.88. Found: C, 60.60; H, 6.65; N, 6.08.

R(-) N-Carbethoxy-N'-(1,2,3,4-tetrahydro-1-naphthalenyl)homopiperazine was obtained as follows:

A dry 100 ml 3-necked flask equipped with a condenser, addition funnel and magnetic stirring bar under a nitrogen atmosphere was charged with of R(-) N-(1,2,3,4-tetrahydro-1-naphthalenyl)homopiperazine (1.1 g; 4.78 mmol) and methylene chloride(19 ml). Triethylamine (0.80 ml; 5.74 mmol) was added and the flask was cooled in a Dry Ice/acetone bath. Ethyl chloroformate (0.50 ml; 5.23 mmol) in methylene chloride (9 ml) was added dropwise and the mixture was allowed to warm to ambient temperature slowly. After stirring overnight the content of the flask was partitioned between water and methylene chloride, the organic phase was washed with brine and the solution was dried with magnesium sulphate. Filtration and removal of solvent gave an yellow oil (1.50 g), homogeneous by tlc (silica gel, ethyl acetate); $^1$H-nmr δ 1.24–1.28 (t, 3H), 4.11–4.18 (q, 2H), 7.03–7.26 (m, 3H), 7.71–7.73 (d, 1H).

EXAMPLE 7

1-Methyl-4-(5-methoxy-1,2,3,4-tetrahydro-1-naphthalenyl)homopiperazine

A 50 ml 3-necked flask equipped with a condenser, addition funnel, mechanical stirrer and under a nitrogen atmosphere was charged with a solution of N-methylhomopiperazine (5.40 g; 47 mmol) in DMF (31 ml). Potassium iodide (8.86 g) was added followed by the addition of a solution of 1-chloro-5-methoxy-1,2,3,4-tetrahydronaphthalene (4.63 g; 23.5 mmol) in DMF (19 ml) over 5 minutes. This solution was then heated at 68° C. for 20 hours and the solvent was removed in vacuo. The resulting concentrate was diluted with water (100 ml) and extracted with four times with ethyl acetate which was washed with brine and dried with sodium sulphate. Filtration and evaporation of solvent gave a yellow oil (6.41 g). Tlc analysis (silica gel, 1:1 $CHCl_3:CH_3OH$) indicated a major component with $R_f$ 0.21 and some impurities at the solvent front. This oil was kugelrohr distilled and the major fraction was collected at (air bath temperature) 132–143° C. at 400 mtorr to give the title compound; $^1$H nmr δ 2.35 (s, 3H), 3.81 (s, 3H), 3.82–3.92(m, 1H), 6.75–6.77 (d, 1H), 7.12–7.17 (t, 1H), 7.42–7.45 (d, 1H).

A solution of the above base (4.44 g) in ethanol (44 ml), was treated with saturated ethanolic HCl (44 ml). While stirring, diethyl ether (120 ml) was added portionwise, resulting in the slow separation of a white solid. After standing this solid was collected by filtration and dried at 62° C. in vacuo to yield the dihydrochloride salt of the title compound (5.53 g) mp 172.2–176.6° C. Anal; Calcd. for $C_{17}H_{26}N_2O.2HCl.0.5H_2O$: C, 57.30; H, 8.20; N, 7.86; Cl, 19.90. Found: C, 57.44; H, 8.50; N, 7.36; Cl, 20.00.

1-Chloro-5-methoxy-1,2,3,4-tetrahydronaphthalene was prepared as follows:

A 3-necked flask equipped with a condenser, addition funnel, mechanical stirrer and under an inert atmosphere was charged with 5-methoxy-1,2,3,4-tetrahydro-1-naphthol (8.70 gm; 48.8 mmol) [available commercially and also via reduction of 5-methoxy-1-tetralone] in dry diethyl ether (145 ml). Pyridine (1.0 g) was added while stirring at room temperature. A solution of thionyl chloride (19.6 ml; 268 mmol) in ether (52 ml) was then added dropwise in 10 minutes and stirring continued overnight. The reaction mixture was then poured into ice-water (500 ml) and the organic phase was separated. The aqueous phase was extracted once more with diethyl ether and the combined organic extract was dried with sodium sulphate. Filtration and removal of solvent in vacuo gave a yellow solid (9.60 g). This material was used without further purification.

EXAMPLE 8

N-(5-Methoxy-1,2,3,4-tetrahydro-1-naphthalenyl)homopiperazine

A 500 ml 3-necked flask equipped with a condenser, nitrogen inlet, thermometer and mechanical stirrer was charged with homopiperazine (64.4 gm; 643 mmol) and DMAC (150 ml). Potassium iodide (4.7 g) was added followed by the addition in one portion of a solution of 1-chloro-5-methoxy-1,2,3,4-tetrahydronaphthalene (25.3 g; 129 mmol) in DMAC (100 ml). This solution was then heated overnight at 68° C. After transferring the contents to a single-necked flask, the solvent was removed on a rotary evaporator under high vacuum using a water bath at 40° C. The resulting concentrate was partitioned between water (400 ml) and ethyl acetate (400 ml) and the aqueous layer was again extracted several times with ethyl acetate, washed with brine and dried with magnesium sulphate.

Filtration and evaporation of solvent gave a residue which by proton nmr was free of the starting chloride. This residue was purified by column chromatography on silica gel (1500 ml) with gradient elution (addition of 10% $NH_4OH$ in methanol in increments to $CH_2Cl_2$) to yield the title compound (29 g). Tlc analysis (silica gel, 89:10:1 $CH_2Cl_2$:$CH_3OH$: $NH_4OH$) indicated a single component with $R_f$ 0.38; $^1H$ nmr δ 3.81 (s, 3H, $OCH_3$), 3.90–4.04(m, 1H, benzylic CHN), 6.67–6.69 (d, 1H), 7.11–7.16 (t, 1H), 7.41–7.45 (d, 1H).

EXAMPLE 9

S(+) N-(5-Methoxy-1,2,3,4-tetrahydro-1-naphthalenyl)homopiperazine

S(+) N-(5-Methoxy-1,2,3,4-tetrahydro-1-naphthalenyl)homopiperazine was obtained as the first material to elute on subjecting racemic material, prepared as in Example 8, to preparative Chiral Pak AD HPLC resolution using a hexane/ethanol mixture with modification with diethylamine. The enantiomeric purity was determined on an analytical scale using hexane:ethanol:diethylamine (97.5:2.5:0.1, v/v) and detection at 220 nm. The solution containing this enantiomer was concentrated using a rotary evaporator to give the title compound (2.42 g), $[\alpha]_D^{22}$+88.4° (c=1.07, methanol); 98.4% ee.

To a solution of this base (1.0 g; 4.35 mmol) in ethanol (10 ml) was added by pipette a solution of maleic acid (1.0 g) in ether (35 ml) which resulted in the formation of a gum. Trituration afforded a white precipitate. This solid was collected by filtration and dried in a drying pistol (50° C., 100 mtorr) to yield the dimaleate salt of the title compound (1.57 g), mp 113.5–115.5° C. Anal. Calcd. for $C_{16}H_{24}N_2O.2C_4H_4O_4.0.5H_2O$: C, 56.43; H, 6.79; N, 5.72. Found: C, 56.56; H, 6.53; N, 5.29.

EXAMPLE 10

S(+) 1-Methyl-4-(5-methoxy-1,2,3,4-tetrahydro-1-naphthalenyl)homopiperazine

A dry 100 ml 3-necked flask equipped with a condenser, addition funnel and magnetic stirring bar was charged with lithium aluminum hydride (0.45 g; 11.8 mmol) and dry THF (15 ml) under a nitrogen atmosphere. S(+) N-Carbethoxy-N'-(5-methoxy-1,2,3,4-tetrahydro-1-naphthalenyl)homopiperazine (1.65 g; 5.0 mmol) in THF (15 ml) was added dropwise and the solution was heated to reflux for 2.5 hours and cooled to ambient temperature. Saturated sodium sulphate (15 ml) was added dropwise at a rate amenable to maintaining control of the reaction and the content of the flask was filtered through diatomaceous earth and dried ($MgSO_4$). Filtration and removal of solvent in vacuo gave a yellow oil (1.15 g) which was kugelrohr distilled to give the title compound (1.05 g), bp (air bath temperature) 110–120° C. at 90 mtorr, homogeneous by tlc (silica gel, $CH_3OH$:$CH_2Cl_2$:$NH_4OH$ 10:89:1), $R_f$ 0.27; $^1H$-nmr δ 2.36 (s, 3H), 3.80–3.86 ($OCH_3$ and benzylic CHN), 6.66–6.68 (d, 1H), 7.10–7.16 (t, 1H), 7.41–7.44(d, 1H); $[\alpha]_D^{22}$+69.1° (c=0.825, methanol).

To a solution of the base (0.91 g) in ethanol (25 ml) was added by pipette a solution of maleic acid (1.0 g) in ether (40 ml). Upon completion of the addition. a white precipitate formed. This solid was collected by filtration and was dried overnight in a drying pistol (50° C. at 100 mtorr) to yield the dimaleate salt of the title compound (1.69 g), mp 125.5–126; $^1H$-nmr (300 MHz, $CD_3OD$) δ 6.26–6.31 (CH═CH, maleic acid), 6.75–6.77 (1H), 7.12–7.17 (1H), 7.29–7.33 (1H): $[\alpha]_D^{22}$+41° (c=0.245, methanol). Anal: Calcd. for $C_{17}H_{26}N_2O.2C_4H_4O_4$: C, 59.29; H, 6.76; N, 5.53. Found C, 59.51; H, 7.06; N, 5.39. S(+) N-Carbethoxy-N'-(5-methoxy-1,2,3,4-tetrahydro-1-naphthalenyl)homopiperazine was obtained as follows:

A dry 100 ml 3-necked flask equipped with a condenser, addition funnel and magnetic Stirring bar under a nitrogen atmosphere was charged with S(+) N-(5-methoxy-1,2,3,4-tetrahydro-1-naphthalenyl)homopiperazine (1.3 g; 5.0 mmol) and methylene chloride (19 ml). Triethylamine (0.90 ml; 6.45 mmol) was added and the flask was cooled in a Dry Ice/acetone bath. Ethyl chloroformate (0.55 ml; 5.75 mmol) in methylene chloride (10 ml) was added dropwise and the mixture was allowed to warm to ambient temperature slowly. After stirring overnight, the content of the flask was partitioned between water and methylene chloride, the organic phase was washed with brine and the solution was dried with magnesium sulphate. Filtration and removal of solvent gave an yellow oil (1.67 g), homogeneous by tlc (silica gel, ethyl acetate), $R_f$ 0.74; $^1H$-nmr δ 1.23–1.28 (t, $OCH_2CH_3$), 3.81 (s, $OCH_3$), 4.11–4.18 (q, $OCH_2CH_3$), 6.67–6.69 (d, 1H), 7.10–7.16 (t, 1H), 7.36–7.39(d, 1H).

EXAMPLE 11

R(−) N-(5-Methoxy-1,2,3,4-tetrahydro-1-naphthalenyl)homopiperazine

R(−) N-(5-methoxy-1,2,3,4-tetrahydro-1-naphthalenyl)homopiperazine was obtained as the second material to elute on subjecting racemic material, prepared as in Example 8, to preparative Chiral Pak AD HPLC resolution using a hexane/ethanol mixture with modification with diethylamine. The solution containing this enantiomer was concentrated using a rotary evaporator to give the title compound (2.95 g).

EXAMPLE 12

R(−) 1-Methyl-4-(5-methoxy-1,2,3,4-tetrahydro-1-naphthalenyl)homopiperazine

A dry 100 ml 3-necked flask equipped with a condenser, addition funnel and magnetic stirring bar was charged with lithium aluminum hydride (0.30 g; 7.90 mmol) and dry THF (10 ml) under a nitrogen atmosphere. R(−) Carbethoxy-N'-(5-methoxy-1,2,3,4-tetrahydro-1-naphthalenyl) homopiperazine (1.25 g; 3.26 mmol) in THF (15 ml) was added dropwise and the solution was heated to reflux for 2.5 hours and cooled to ambient temperature. Saturated sodium sulphate (10 ml) was added dropwise at a rate amenable to maintaining control of the reaction and the content of the flask was filtered through diatomaceous earth and dried (MgSO$_4$). Filtration and removal of solvent in vacuo gave an oil (0.90 g) which was kugelrohr distilled to give the title compound (0.74 g), bp (air bath temperature) 125–140° C. at 80 mtorr, homogeneous by tlc (silica gel, CH$_3$OH:CH$_2$Cl$_2$:NH$_4$OH 10:89:1); $^1$H-nmr δ 2.36 (s, 3H), 3.82–3.88 (OCH$_3$ and benzylic CHN), 6.66–6.69 (d, 1H), 7.11–7.16 (t, 1H), 7.42–7.45(d, 1H); $[α]_D^{22}$ −66.6° (c=0.72, methanol).

To a solution of the base (0.73 g) in ethanol (10 ml) was added by pipette a solution of maleic acid (0.80 g) in ether (40 ml). Upon completion of the addition, a white precipitate formed. This solid was collected by filtration and was dried overnight in a drying pistol (50° C. at 90 mtorr) to yield the dimaleate salt of the title compound (1.17 g), mp 124.8–125.4; $^1$H-nmr (300 MHz, CD$_3$OD) δ 4.02 (s, 3H), 6.52 (4H, CH=CH maleic acid), 6.99–7.01 (1H), 7.36–7.41 (1H), 7.55–7.58 (1H): Anal: Calcd. for C$_{17}$H$_{26}$N$_2$O.2C$_4$H$_4$O$_4$: C, 59.29; H, 6.76; N, 5.53. Found: C, 59.39; H, 7.01; N, 5.39. R(−) N-Carbethoxy-N'-(5-methoxy-1,2,3,4-tetrahydro-1-naphthalenyl)homopiperazine was obtained as follows:

A dry 100 ml 3-necked flask equipped with a condenser, addition funnel and magnetic stirring bar under a nitrogen atmosphere was charged with R(−) N-(5-methoxy-1,2,3,4-tetrahydro-1-naphthalenyl)homopiperazine (1.8 g; 6.92 mmol) and methylene chloride (15 ml). Triethylamine (1.30 ml; 9.32 mmol) was added and the flask was cooled in a Dry Ice/acetone bath. Ethyl chloroformate (0.80 ml; 8.37 mmol) in methylene chloride (10 ml) was added dropwise and the mixture was allowed to warm to ambient temperature slowly. After stirring overnight, the content of the flask was partitioned between water and methylene chloride, the organic phase was washed with brine and the solution was dried with magnesium sulphate. Filtration and removal of solvent gave a brown oil (2.10 g). This material was purified by column chromatography on silica gel with ethyl acetate elution to give an amber oil (1.3 g); $^1$H-nmr δ1.23–1.28 (t, OCH$_2$CH$_3$), 3.81 (s, OCH$_3$), 4.11–4.18 (q, OCH$_2$CH$_3$), 6.67–6.70 (d, 1H), 7.08–7.16 (t, 1H), 7.38–7.40(d, 1H). $[α]_D^{22}$ −59.5° (c=0.92, methanol).

EXAMPLE 13

1-Isopropyl-4-(1,2,3,4-tetrahydro-1-naphthalenyl)homopiperazine

A 100 ml 3-necked flask under nitrogen atmosphere was charged sequentially with N-(1,2,3,4-tetrahydro-1-naphthalenyl)homopiperazine (0.73 g; 3.2 mmol) in THF (20 ml), methanol (10 ml) and acetone (3.3 ml; 45 mmol). To this stirred solution, sodium cyanoborohydride (0.30 g; 4.75 mmol) was added as a solid followed by acetic acid (0.24 ml; 4.2 mmol). After stirring at ambient temperature for 45 minutes, tlc analysis (silica gel, 9:1 CHCl$_3$:CH$_3$OH) of an aliquot revealed the absence of starting amine (R$_f$ 0.03) and the presence of a major component with R$_f$ 0.16. The content of the flask was then concentrated in vacuo. The residue was treated with aqueous sodium bicarbonate and extracted several times with ethyl acetate which was then dried with sodium sulphate. Filtration and removal of solvent in vacuo gave an oil which was subjected to high vacuum for four hours at ambient temperature to yield the title compound (0.87 g); tlc (ibid), homogeneous, R$_f$ 0.16; $^1$H nmr δ 1.01–1.05 (6H), 3.88–3.92 (m, 1H), 6.98–7.22 (m, 3H), 7.77–7.79 (1, H). Anal: Calcd. for C$_{18}$H$_{28}$N$_2$; C, 79.36; H, 10.36; N, 10.28. Found: C, 79.46; H, 10.12; N, 10.08.

The above base (0.67 g) was dissolved in ethanolic HCl (7 ml) and was treated with ether (~45 ml) portionwise to the cloud point. On standing, only a gum separated. Trituration resulted in the formation of a white solid which was collected by filtration and dried in vacuo (65° C. at 20 mtorr) to give the dihydrochloride salt of the title compound (0.66 g), mp 149.5–151° C. (hygroscopic). Anal: Calcd. for C$_{18}$H$_{28}$N$_2$.2HCl.0.66H$_2$O: C, 58.06; H, 8.93; N, 7.52. Found: C, 58.11; H, 8.87; N, 7.30.

EXAMPLE 14

S(+) 1-Isopropyl-4-(1,2,3,4-tetrahydro-1-naphthalenyl)homopiperazine

A 25 ml 3-necked flask under nitrogen atmosphere was charged sequentially with S(+) N-(1,2,3,4-tetrahydro-1-naphthalenyl)homopiperazine (0.30 g; 1.3 mmol) in THF (8 ml), methanol (4 ml) and acetone (1.1 ml; 18 mmol). To this stirred solution, sodium cyanoborohydride (0.12 g; 2.0 mmol) was added as a solid followed by acetic acid (0.10 ml; 1.8 mmol). After stirring at ambient temperature for 45 minutes, tlc analysis (silica gel, 9:1 CHCl$_3$:CH$_3$OH) of an aliquot revealed the absence of starting amine. The content of the flask was then concentrated in vacuo. The residue was treated with aqueous sodium bicarbonate and extracted several times with ethyl acetate which was then dried with sodium sulphate. Filtration and removal of solvent in vacuo gave an oil (0.50 g) which was kugelrohr distilled to yield the title compound (0.31 g), bp (air bath temperature) 148–152° C. at 160 mtorr; tlc (ibid), R$_f$ 0.18. $[α]_D^{22}$+80° (c=1.00, methanol).

The above base (0.25 g) was dissolved in ethanol (5.5 ml) and was treated with a saturated solution of maleic acid in ether (11 ml) and left at ambient temperature. On prolonged standing, a solid very slowly separated. This was collected by filtration and dried in vacuo (65° C. at 20 mtorr) to give the dimaleate salt of the title compound (0.28 g), mp 115.5–116.2° C. Anal: Calcd. for C$_{18}$H$_{28}$N$_2$.2C$_4$H$_4$O$_4$: C, 61.89; H, 7.19; N, 5.55. Found: C, 61.44; H, 7.16; N, 5.52.

EXAMPLE 15

N-(6-Fluoro-1,2,3,4-tetrahydro-1-naphthalenyl)homopiperzine

Under nitrogen atmosphere, a 3-necked 500 ml round-bottomed flask was charged with homopiperazine (20 mg), DMF (130 ml) and potassium iodide (0.35 g). A solution of 7.70 g (41.7 mmol) of 1-chloro-6-fluoro-1,2,3,4- tetrahydronaphthalene in 39 ml of DMF was added over a five minute period. The mixture was stirred at 55°–60° C. for two hours and then at ambient temperature overnight. Tlc analysis on silica gel (diethyl ether:hexane 5:95) showed the absence of the starting halide, $R_f$ 0.77. Most of the DMF was then removed in vacuo (35° C., 0.6 torr) using a rotary evaporator. The residue was treated with 300 ml of water and extracted with ethyl acetate which was then dried ($MgSO_4$). Filtration and removal of solvent in vacuo gave a yellow oil which was kugelrohr distilled to give the title compound, (8.63 g), bp (air bath temperature) 155°–166° C. at 0.26 torr, as a viscous yellow oil. $^1$H NMR (300 MHz, $CDCl_3$) δ 3.86 (t, 1H, ArCHN), 6.78 (dd, 1H), 6.85 (m, 1H), 7.75 (m, 1H). Anal: Calcd. for $C_{15}H_{21}FN_2$: C, 72.55; H, 8.52; N, 11.28. Found: C, 72.05; H, 8.53; N. 10.95. 1-Chloro-6-fluoro-1,2, 3,4-tetrahydronaphthalene was prepared as follows:

To a solution of 7.02 g (42.2 mmol) of 6-fluoro-1,2,3,4-tetrahydro-1-naphthol and 0.92 ml of pyridine in 130 ml of ether under nitrogen was added 16.9 ml (232 mmol) of thionyl chloride in 44 ml of ether over ten minutes. After stirring overnight at ambient temperature, tlc analysis on silica gel (ether:hexane 5:95) indicated the absence of the starting alcohol. The mixture was added to 200 g of ice, diluted with more ether and the ether extract was washed with water and brine and dried ($MgSO_4$). Filtration and removal of the solvent invacuo gave 7.73 g of a yellow oil. Tlc analysis indicated a major component at $R_f$ 0.77 and a minor component at $R_f$ 0.85. $^1$H NMR (300 MHz, $CDCl_3$) δ 5.3 (t, 1H, ArCHCl), 7.4 (m, 1H), 6.85 (m, 1H), 6.78 (dd, 1H). A minor amount of 3,4-dihydro-6-fluoronaphthalene was indicated as the impurity. This material was used without further purification.

EXAMPLE 16

1-Methyl-4-(6-fluoro-1,2,3,4-tetrahydro-1-naphthalenyl)homopiperazine

A 20 ml round bottom flask under nitrogen atmosphere was charged with 0.47 g (1.9 mmol) of the homopiperazine prepared in Example 15, 1.2 ml of water and 0.92 ml of 98% formic acid. After stirring for five minutes, 0.34 ml (4.6 mmol) of 37% formaldehyde was added and the mixture was heated in an oil bath at 70° C. After one hour tlc analysis on silica gel ($CHCl_3$:$CH_3OH$ 95:5) indicated the absence of the starting amine ($R_f$, origin) and components with $R_f$s 0.10 . 0.72 and 0.95. The mixture was diluted with water and extracted several times with ether. The aqueous extract was made alkaline with solid potassium carbonate and extracted with ethyl acetate which was dried ($MgSO_4$). Filtration and removal of solvent in vacuo gave 45 mg of an oil (lower $R_f$). $^1$H NMR (300 MHz, $CDCl_3$) δ 2.34 (s, 3H), 3.82 (t, 1H, ArCHN), 6.75 (dd, 1H), 6.85 (m, 1H) 7.73 (t, 1H).

This material in 1.4 ml of ethanol was treated with 2.8 ml of a saturated solution of maleic acid in diethyl ether. Since no precipitate formed on standing, the solution was concentrated to give a gum. Trituration with ether and decantation resulted in the formation of a solid which was dried in vacuo at 55° C. to give 39 mg, mp 78.8°–79.5° C. Anal: Calcd. for $C_{16}H_{23}FN_2 \cdot 2C_4H_4O_4 \cdot 0.75H_2O$: C, 56.74; H, 6.45; N. 5.51. Found: C, 56.88; H, 6.32; N, 5.28.

EXAMPLE 17

S(+) N-(6-Fluoro-1,2,3,4-tetrahydro-1-naphthalenyl)homopiperazine

S(+) N-(6-Fluoro-1,2,3,4-tetrahydro-1-naphthalenyl)homopiperazine was obtained as the first material to elute on subjecting racemic material (approximately 3.5 g), prepared as in Example 15, to preparative Chiral Pak AD HPLC resolution using a hexane/ethanol mixture with modification with diethylamine. The enantiomer purity was determined on an analytical scale using hexane:ethanol:diethylamine (90:10:0.10, v/v) and detection at 220 nm. The solution containing this enantiomer was concentrated using a rotar evaporator. The residue was kugelrohr distilled to give 1.4 g of a colorless oil, bp (air bath temperature) 110°–120° C. at 120 mtorr, $[\alpha]_D^{22}$+93.5° (c=1.46, methanol); >99% ee. Anal: Calcd. for $C_{15}H_{21}FN_2$: C, 72.55; H, 8.52; N, 11.28. Found: C, 72.14; H, 8.44; N, 11.11.

EXAMPLE 18

S(+) 1-Methyl-4-(6-fluoro-1,2,3,4-tetrahydro-1-naphthalenyl)homopiperazine

S(+) N-Carbethoxy-N'-(6-fluoro-1,2,3,4-tetrahydro-1-naphthalenyl)homopiperazine (1.30 g: 4.00 mmol) was reduced with lithium aluminum hydride (0.32 g; 8 mmol) in THF as in Example 4. The yellow oil was kugelrohr distilled to give the title compound (0.88 g), bp (air bath temperature) 125° C. at 150 mtorr., homogeneous by tlc (silica gel, $CH_3OH$:$CH_2Cl_2$:$NH_4OH$ 10:89:1), $R_f$ 0.44; $[\alpha]_D^{22}$+92.1° (c=0.467, methanol). A solution of this material in 5 ml of ethanol was treated with saturated ethereal HCl to form a white solid which was collected by filtration and dried in vacuo (65° C., 200 mtorr) overnight to give 1.04 g, mp 230.6°–231.6° C. Anal: Calcd. for $C_{16}H_{23}FN_2 \cdot 2HCl \cdot 0.1H_2O$: C, 57.00; H, 7.53: N, 8.31. Found: C, 56.73; H, 7.41; N, 7.94. S(+) N-Carbethoxy-N'-(6-fluoro-1,2,3,4-tetrahydro-1-naphthalenyl)homopiperazine was obtained as follows:

S(+) N-(6-fluoro-1,2,3,4-tetrahydro-1-naphthalenyl)homopiperazine (1.0 g; 4.03 mmol), triethylamine (0.70 ml; 5.02 mmol) and ethyl chloroformate (0.50 ml; 5.2 mmol) were reacted in methylene chloride as in Example 4 to give a yellow oil (1.30 g), homogeneous by tlc (silica gel, ethyl acetate), $R_f$ 0.83; $^1$H NMR (300 MHz, $CDCl_3$) δ 4.11–4.18 (q, 2H, $OCH_2CH_3$).

EXAMPLE 19

R(−) N-(6-Fluoro-1,2,3,4-tetrahydro-1-naphthalenyl)homopiperazine

R(−) N-(6-Fluoro-1,2,3,4-tetrahydro-1-naphthalenyl)homopiperazine was obtained as the second material to elute on subjecting racemic material, prepared as in Example 15, to preparative Chiral Pak AD HPLC resolution using a hexane/ethanol mixture with modification with diethylamine. The enantiomeric purity was determined on an analytical scale using hexane:ethanol:diethylamine (90:10:0.10, v/v) and detection at 220 nm. The solution containing this enantiomer was concentrated using a rotary evaporator and the residue was kugelrohr (as in example 17) to give the titled compound (1.38 g), $[\alpha]_D^{22}$−88.6° (c=2.01, methanol); >99% ee. Anal: Calcd. for $C_{15}H_{21}FN_2$: C, 72.55; H, 8.52; N, 11.28. Found: C, 72.05; H, 8.46; N, 11.13.

EXAMPLE 20

R(−) 1-Methyl-4-(6-fluoro-1,2,34-tetrahydro-1-naphthalenyl)homopiperazine

In an analogous method to Example 18, R(−) N-Carbethoxy-N'-(6-fluoro-1,2,3,4-tetrahydro-1-naphthalenyl)homopiperazine (1.60 g) in THF (15 ml) was reacted with lithium aluminium hydride (0.40 g) in THF (15 ml). Additional 0.85 g of lithium aluminium hydride was added to complete the reaction. Kugelrohr distillation gave the title compound (1.053 g), bp (air bath temperature) 110° C. at 100 mtorr; $[\alpha]_D^{22}$ −85.3° (c=1.77, methanol).

Treatment of a solution of 1.0 g of this base in 7 ml of ethanol with saturated ethereal HCl resulted in the formation of a white solid which was collected by filtration and dried invacuo (61° C., 100 mtorr) overnight to give 1.12 g, mp 229°–230° C. Anal: Calcd. for $C_{16}H_{23}FN_2 \cdot 2HCl$: C, 57.32; H, 7.52: N. 8.35. Found: C, 56.92; H, 7.35; N, 8.60. R(−) N-Carbethoxy-N'-(6-fluoro-1,2,3,4-tetrahydro-1-naphthalenyl)homopiperazine was obtained from R(−) N-(6-fluoro-1,2,3,4-tetrahydro-1-naphthalenyl)homopiperazine (1.3 g) in a manner analogous to that of Example 18, giving a viscous oil (1.6 g), homogeneous by tlc (silica gel. ethyl acetate). $^1$H NMR δ 4.11–4.18 (q, 2H, OCH$_2$CH$_3$).

EXAMPLE 21

1-Methyl-4-(6-bromo-1,2,3,4-tetrahydro-1-naphthalenyl)homopiperazine

N-Methylhomopiperazine (2.31 g; 20.2 mmol) and potassium iodide (0.35 g; 2.2 mmol) in DMF (13 ml) were reacted with 1-chloro-6-bromo-1,2,3,4-tetrahydronapthalene (2.48 g; 10.1 mmol) in DMF (8 ml) as in Example 15. The yellow oil was kugelrohr distilled to give the title compound, 1.47 g, bp (air bath temperature) 152°–165° C. at 0.10 torr; $^1$H NMR (300 MHz, CDCl$_3$) δ 2.38 (s, 3H, NCH3), 3.81 (t, 1H, ArCHN), 7.19 (s, 1H), 7.25 (d, 1H), 7.64 (d, 1H). Anal: Calcd. for $C_{16}H_{23}BrN_2$: C, 59.45; H, 7.17; N, 8.67. Found: C, 59.40; H, 7.02; N, 8.30. 1-Chloro-6-bromo-1,2,3,4-tetrahydronaphthalene was prepared as follows:

A solution of 6-bromo-1,2,3,4-tetrahydro-1-naphthol (7.10 g; 31.3 mmol) and pyridine (0.68 ml) in ether (95 ml) under nitrogen was treated with thionyl chloride (12.6 ml; 172 mmol) in ether (33 ml) as in Example 15 to give a yellow oil (7.3 g). Tlc analysis (ibid) indicated a major component at $R_f$ 0.68 and a very minor component at $R_f$ 0.73; $^1$H NMR (300 MHz, CDCl$_3$) δ 5.24 (m, 1H, ArCHCl), 7.19–7.30 (3H). A minor amount of 3,4-dihydro-6-bromonaphthalene was indicated as an impurity. This material was used without further purification. 6-Bromo-1,2,3,4-tetrahydro-1-naphthol was prepared as follows:

A one liter three-necked roundbottom flask under a nitrogen atmosphere was charged with 1.07 g (49.1 mmol) of lithium borohydride and 106 ml of ether and the stirred suspension was cooled to −75° C. (Dry Ice/acetone). A solution of 7.0 g (31.1 mmol) of 6-bromo-1-tetralone in 336 ml of ether was added over a 15 minute period and the mixture was allowed to warm to 0° C. Additional lithium borohydride, 0.6 g (27 mmol), was added and stirring continued at 0° C. for another fifteen minutes at which time tlc analysis on silica gel (ether:hexane 1:4) indicated a major component with $R_f$ 0.21 and absence of the starting ketone ($R_f$ 0.45). Ice was added to the mixture which was then stirred overnight. The ether phase was separated, dried (MgSO4) and concentrated invacuo to give 7.04 g of a colorless oil which solidified. $^1$H NMR (300 MHz, CDCl$_3$) δ 1.7–2.1 (m, 4H), 2.66–2.83 (m, 2H), 4.72 (t, 1H, ArCHOH), 7.26 (s, 1H), 7.31 (over lapping singlets, 2H).

EXAMPLE 22

N-(6-Bromo-1,2,3,4-tetrahydro-1-naphthalenyl) homopiperazine

A solution of of homopiperazine (2.96 g; 29.6 mmol) and potassium iodide (0.05 g; 0.28 mmol) in DMF (17 ml) was treated with 1-chloro-6-fluoro-1,2,3,4-tetrahydronapthalene (1.45 g; 5.91 mmol) in DMF (5 ml) as in Example 15. Kugelrohr distillation gave the title compound as a yellow oil, 0.98 g, bp (air bath temperature) 165°–180° C. at 0.10 torr; homogeneous by tlc on silica gel (CHCl$_3$:CH$_3$OH 9:1), $R_f$ 0.07; $^1$H NMR (300 MHz, CDCl$_3$) δ 2.97 (t, 2H, ArCH2), 3.81 (t, 1H, ArCHN), 7.19 (s, 1H), 7.25 (dd, 1H), 7.66 (d, 1H). Anal: Calcd. for $C_{15}H_{21}BrN_2$: C, 58.26; H, 6.84; N, 9.06. Found: C, 58.30; H, 6.58; N, 8.21.

EXAMPLE 23

1-Methyl-4-(6-formyl-1,2,3,4-tetrahydro-1-naphthalenyl)homopiperazine

Under nitrogen atmosphere, a dry 3-necked 50 ml round-bottomed flask was charged with 2.31 g (20.2 mmol) of 1-methyl-4-(6-bromo-1,2,3,4-tetrahydro-1-naphthalenyl) homopiperazine and 8 ml of anydrous THF and was cooled to −75° C. (Dry Ice/acetone). To this solution was added dropwise 4.1 ml (6.9 mmol, 2.18 equivalents) of t-butyllithium (1.7M solution in pentane) over a ten minute period, followed by stirring for an additional ten minutes. Anhydrous DMF, 25 ml, was added rapidly resulting in the temperature rising to −40° C. The solution was again cooled to −75° C. and was allowed to spontaneously warm to room temperature. The content of the flask was added to water and acidified with 1N HCl to pH 2. After five minutes this solution was made alkaline with potassium carbonate and extracted several times with ether. The combined ether extract was dried (MgSO$_4$), filtered and concentrated invacuo to yield 0.82 g of a yellow oil. Proton NMR analysis (300 MHz) indicated that this material was a 6:1 mixture of the title compound and 1-methyl-4-(1,2,3,4-tetrahydro-1-naphthalenyl)homopiperazine. A portion, 0.41 g, was subjected to kugelrohr distillation with temperature maintained at 100°–102° C. at 0.06 torr. This resulted in a distillate which was a mixture of the two components. The residual material was the pure title compound, 0.33 g; $^1$H-NMR (300 MHz, CDCl$_3$) δ 3.88–3.93 (m, 1H, ArCHN), 7.56 (s, 1H), 7.65–7.68 (d, 1H), 7.97–8.02 (d, 1H), 9.50 (s, 1H, CHO).

EXAMPLE 24

1-Methyl-4-(6-vinyl-1,2,3,4-tetrahydro-1-naphthalenyl)homopiperazine

A dry flask under nitrogen was charged with 0.25 g (0.69 mmol) of methyltriphenyl phosphonium bromide and 2.1 ml of anhydrous THF. To this suspension at ambient temperature was added 0.30 ml (0.69 mmol) of a 2.3 M solution of n-butyllithium in hexane. This was followed by the addition of a solution of 0.18 g (0.67 mmol) of 1-methyl-4-(6-formyl-1,2,3,4-tetrahydro-1-naphthalenyl)homopiperazine in 1.4 ml THF. After two hours, analysis by $^1$H-NMR of a worked-up aliquot revealed the presence of the desired product (vinyl proton resonances) as well as residual aldehyde (CHO resonance). A second portion of the triphenylphosphonium ylid (0.070 mmol) was generated in 4 ml THF and added to the mixture containing the residual aldehyde. After four hours, analysis by $^1$H-NMR of a worked-up aliquot indicated only a trace of aldehyde. The reaction mixture was concentrated invacuo to semisolid which was treated with water and extracted several times with ether. The combined ether extract was dried (MgSO$_4$), filtered and concentrated invacuo to a semisolid, 0.34 g. This material was triturated with hexane, filtered and the hexane was removed invacuo. The resulting residue was again titurated with hexane, filtered and concentrated invacuo to give the title compound, 0.18 g, as a yellow oil; $^1$H-NMR(300 Hz, CDCl$_3$) δ 5.17–5.20 (1H, d), 5.68–5.74 (1H, d), 6.62–6.71 (1H, q).

EXAMPLE 25

1-Methyl-4-(6-ethyl-1,2,3,4-tetrahydro-1-naphthalenyl)homopiperazine

A solution of 0.17 g of 1-methyl-4-(6-vinyl-1,2,3,4-tetrahydro-1-naphthalenyl)homopiperazine in 2 ml of THF was hydrogenated at atmospheric pressure using 0.08 g of 10% Palladium-on-carbon as catalyst. After five hours, the mixture was filtered and the solvent was removed invacuo. Kugelrohr distillation of this oil gave 0.14 g of a colorless oil, bp (air bath temperature) 116°–122° C. at 40 mmtorr, essentially homogeneous by tlc on silca gel (CHCl$_3$:CH$_3$OH 9:1). R$_f$ 0.15.

A portion of this material, 0.083 g, in 2.5 ml of ethanol was treated dropwise with 5.5 ml of a saturated solution of maleic acid in diethyl ether to form a precipitate. This heterogeneous solution was diluted with 4 ml of diethyl ether and was left at ambient temperature overnight. The white solid was collected by filtration, washed with ether and dried invacuo to give 0.050 g, mp 131.5°–132.8° C.; $^1$H-NMR (300 MHz, d$_6$-DMSO) δ 1.31–1.81(t, 3H, CH$_3$CH$_2$), 2.89 (s, 3H, NCH$_3$), 3.91 (1H, ArCHN), 6.14 (s, 4H, CH=CH, maleic acid), 6.90 (s, 1H), 6.98–7.00 (d, 1H), 7.59–7.61 (d, 1H). Anal: Calcd. for C$_{18}$H$_{28}$N$_2$.2C$_4$H$_4$O$_4$: C, 61.89; H, 7.19; N, 5.55. Found: C, 61.51; H, 7.08; N, 5.51.

EXAMPLE 26

R(−) N-Isopropyl-N'-(1,2,3,4-tetrahydronaphthalen-4-yl)homopiperazine

R(−) N-(1,2,3,4-tetrahydronaphthalen4-yl)homopiperazine (2.00 g; 8.7 mmol) in THF (50 ml), methanol (25 ml) and acetone (15.5 ml; 174 mmol) was reacted with sodium cyanoborohydride (1.1 g; 17.6 mmol) and acetic acid (1.0 ml) as in Example 14. Kugelrohr distillation gave the title compound (2.29 g), bp (air bath temperature) 165–175° C. at 180 mtorr; [α]$_D^{22}$ −74° (c=0.64, methanol).

The above base (2.25 g) was dissolved in ethanol (10 ml) and was slowly treated with a dispersion of 2.25 g (19.3 mmol) of maleic acid in ether (100 ml), resulting in the formation of a gum. The ether was decanted and the residue was triturated with fresh ether to get a solid. This was collected by filtration and dried invacuo (60° C. at 150 mtorr) to give the dimaleate salt of the title compound (2.55 g), mp 105–106° C.; $^1$H NMR (300 MHz, d$_6$-DMSO) δ 1.23–1.25 (d, 6H), 6.10 (4H, CH=CH, maleic acid). Anal: Calcd. for C$_{18}$H$_{28}$N$_2$.2C$_4$H$_4$O$_4$: C, 61.89; H, 7.19; N, 5.55. Found: C, 61.44; H, 7.14; N, 5.54.

EXAMPLE 27

1-(1,2,3,4-Tetrahydronaphthyl)-4-(3-methylbutyl)homopiperazine

A 250 mL flask was charged with a solution of 1-(1,2,3,4-tetrahydronaphthyl)homopiperazine (2.68 g, 11.6 mmol) in THF (105 mL). Triethylamine (2.20 ml, 3.03 g, 29.9 mmol) and 1-bromo-3-methylbutane (2.00 ml, 1.59 g, 10.5 mmol) were added. The solution was immersed in a 60° C. oil bath for 16 hours during which time a precipitate formed. The resulting mixture was filtered and the filtrate was concentrated to give an orange oil. This crude product was purified by column chromatography using diethyl ether:hexane:methanol (5:5:1) to obtain the title compound as a yellow oil (2.34 g). $^1$H NMR (CDCl$_3$, 300 MHz) δ 0.89 (d, 6H), 1.39 (m, 2H), 1.54–1.79 (m, 5H), 1.92–2.15 (m, 2H), 2.50 (m, 2H), 2.60–2.80 (m, 10H), 3.90 (m, 1H), 7.02–7.18 (m, 3H), 7.77 (d, 2H); m/s: M+H$^+$ 301.

EXAMPLES 28–51

By the method of Example 27, substituting the corresponding bromo compound for 1-bromo-3-methylbutane the following compounds were prepared, wherein (R) and (S) refer o the stereochemistry at the 1-position of the 1,2,3,4-tetrahydronaphthyl ring.

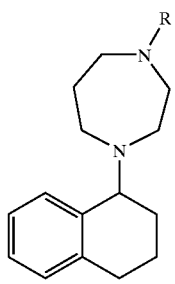

| Examples | R | NMR | m/s M + H$^+$ |
|---|---|---|---|
| 28 | ⋏⋏Ph | 7.76 (d 1H), 7.39–7.11 (m, 8H), 3.57 (t. 1H), 3.16 (t, 1H), 2.91 (t, 1H), 2.81–2.72 (m, 7H), 1.87 (m, 1H), 1.83 (m, 2H), 1.79 (m, 1H), 1.64 (m, 2H), 1.16 (m, 2H) | 335 |
| 29[1] | ⋏⋏⋏Ph | 7.75 (d, 1H), 7.31–7.03 (m, 8H), 3.91 (m, 1H), 2.95 (t, 2H), 2.85–2.72 (m, 14H), 1.98 (m, 2H), 1.86 (m, 2H), 1.64 (m, 2H) | 349 |

-continued

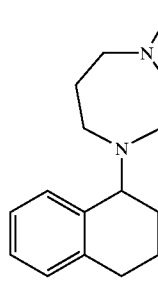

| Examples | R | NMR | m/s M + H⁺ |
|---|---|---|---|
| 30[2,3] | 2,3,4,5,6-pentafluorobenzyl | 7.46 (d, 1H), 7.22–6.98 (m, 3H), 3.88 (m, 1H), 3.85 (s. 2H), 2.83–2.65 (m, 10H), 1.98 (m, 2H), 1.76 (m, 2H), 1.63 (m, 2H) | 411 |
| 31[1] | 4-nitrobenzyl | 8.14 (d, 2H), 7.53 (d, 1H), 7.36 (d, 2H), 7.18–7.03 (m, 3H), 3.92 (m, 1H), 2.91–2.68 (m, 14H), 1.98 (m, 2H), 1.81 (m, 2H), 1.63 (m, 2H) | 380 |
| 32[4] | 2,3-difluorobenzyl | 7.82 (d,1H), 7.18–7.01 (m, 6H), 3.92 (m, 1H), 3.70 (s, 2H), 2.82–2.66 (m, 10H), 2.07–1.93 (m, 2H), 1.78 (m, 2H), 1.66 (m, 2H) | 357 |
| 33[5] | 2,3,5,6-tetrafluoro-4-(trifluoromethyl)benzyl | 7.72 (d, 1H), 7.17–7.08 (m, 3H), 3.88 (m, 3H), 2.83 (m, 2H), 2.75–2.66 (m, 6H), 1.99 (m, 2H), 1.77 (m, 2H), 1.64 (m, 2H), 1.43 (m, 2H) | 461 |
| 34[1] | 2-(trifluoromethyl)benzyl | 7.88 (d, 1H), 7.80 (d, 1H), 7.59 (d, 1H), 7.50 (t, 1H), 7.29 (t, 1H), 7.19–6.98 (m, 3H), 3.93 (m, 1H), 3.83 (s, 2H), 2.82–2.66 (m, 10H), 1.96 (m, 2H), 1.76 (m, 2H), 1.64 (m, 2H) | 389 |
| 35 | 4-tert-butylbenzyl | 7.82 (d, 1H), 7.34–7.26 (m, 4H), 7.17–7.02 (m, 3H) 3.89 (m, 1H), 3.66 (s, 2H), 2.83–2.62 (m, 10H), 2.08–1.95 (m, 2H), 1.86–1.75 (m, 2H), 1.68–1.58 (m, 2H), 1.31 (s, 9H) | 377 |
| 36 | 4-(benzyloxy)benzyl | 7.89 (d, 1H), 7.48–7.26 (m, 5H), 7.25 (d, 2H), 7.16–6.95 (m, 3H), 6.92 (d, 2H), 5.05 (s, 2H), 3.88 (m, 1H), 3.60 (s, 2H), 2.81–2.60 (m, 10H), 2.02 (m, 2H), 1.77–1.58 (m, 4H) | 427 |
| 37[1,6] | —Et | 7.73 (d, 1H), 7.19–7.04 (m, 3H), 3.91 (m, 1H), 2.91 (m, 2H), 2.85–2.67 (m, 10H), 2.08–1.88 (m, 4H), 1.63 (m, 2H), 1.17 (t, 3H) | 259 |
| 38[7] | -n-Pr | 7.74 (d, 1H), 7.20–7.00 (m, 3H), 3.90 (m, 1H), | 273 |

-continued

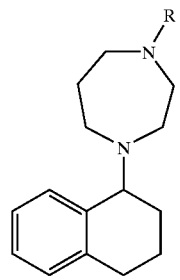

| Examples | R | NMR | m/s M + H+ |
|---|---|---|---|
| 39[7] | -n-Bu | 2.85 (m, 2H), 2.74 (m, 8H), 2.57 (m, 2H), 1.96 (m, 4H), 1.68–1.53 (m, 4H), 1.26 (t, 3H) 7.80 (d, 1H), 7.18–6.91 (m, 3H), 3.93 (m, 1H), 2.84–2.70 (m, 10H), 2.53 (t, 2H), 2.53 (m, 2H), 2.02 (m, 2H), 1.81 (m, 2H), 1.64 (m, 2H), 1.61 (m, 2H) 0.95 (t, 3H) | 287 |
| 40[8,4] | -n-pentyl | 7.73 (d, 1H), 7.22–7.11 (m, 3H), 3.89 (m, 1H), 2.95 (m, 2H), 2.74 (m, 2H), 2.56 (m, 8H), 1.99 (m, 2H), 1.86 (m, 2H), 1.68–1.54 (m, 4H), 1.30 (m, 4H), 0.89 (t, 3H) | 301 |
| 41[9,10] | CH2-cyclopropyl | 7.66 (d, 1H), 7.08–6.92 (m, 3H), 3.78 (m, 1H), 2.77 (t, 2H), 2.73–2.56 (m, 8H), 2.32 (d, 2H), 1.90 (m, 2H), 1.69 (m, 2H), 1.51 (m, 2H), 0.79 (m, 1H), 0.39 (m, 2H), −0.14 (m, 2H) | 285 |
| 42[11,12] | CH2-cyclobutyl | 7.70 (d, 1H), 7.21–7.11 (m, 3H), 3.90 (m, 1H), 2.93 (m, 2H), 2.76–2.52 (m, 12H), 2.08–1.68 (m, 11H) | 299 |
| 43[13,14] | 2-ethylhexyl | 7.77 (d, 1H), 7.21–7.03 (m, 3H), 3.91 (m, 1H), 2.90–2.63 (m, 10H), 2.34 (m, 2H), 2.01 (m, 2H), 1.81–1.72 (m, 2H), 1.69–1.58 (m, 2H), 1.33–1.27 (m, 9H), 0.87 (m, 6H) | 343 |
| 44[15] | (S) -CH2CH2CH2CH2-Ph | 7.76 (d, 1H), 7.34–6.97 (m, 8H), 3.88 (m, 1H), 2.84–2.51 (m, 14H), 2.00 (m, 2H), 1.83–1.61 (m, 6H) | 349 |
| 45[15] | (R) -CH2CH2CH2CH2-Ph | 7.76 (d, 1H), 7.34–6.97 (m, 8H), 3.88 (m, 1H), 2.84–2.51 (m, 14H), 2.00(m, 2H), 1.83–1.61 (m, 6H) | 349 |
| 46[16] | (S) -CH2CH(CH3)2 chain | 7.77 (d, 1H), 7.18–7.03 (m, 3H), 3.90 (m, 1H), 2.85–2.65 (m, 10H), 2.58 (m, 2H), 2.08–1.95 (m, 2H), 1.84 (m, 2H), 1.60 (m, 3H), 1.41 (m, 2H), 0.89 (d, 6H) | 301 |
| 47[16] | (R) | 7.75 (d, 1H), 7.25–6.98 (m, 3H), 3.90 (m, 1H), 2.87–2.67 (m, 10H), 2.58 (m, 2H), 1.99 (m, 2H), 1.84 (m, 2H), 1.61 (m, 3H), 1.43 (m, 2H), 0.90 (d, 6H) | 301 |
| 48[13,17] | (S) 2-ethylhexyl | 7.76 (d, 1H), 7.18–7.02 (m, 3H), 3.88 (m, 1H), 2.82–2.61 (m, 10H), 2.30 (d, 2H), 2.00 (m, 2H), 1.74–1.61 (m, 4H), 1.39–1.21 (m, 9H), 0.86 (m, 6H) | 343 |

-continued

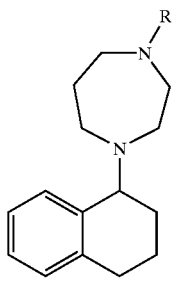

| Examples | R | NMR | m/s M + H+ |
|---|---|---|---|
| 49[13,18] | (R) 2-ethylhexyl | 7.79 (d, 1H), 7.18–7.02 (m, 3H), 3.88 (m, 1H), 2.82–2.61 (m, 10H), 2.30 (d, 2H), 2.01 (m, 2H), 1.74–1.62 (m, 4H), 1.38–1.19 (m, 9H), 0.87 (m, 6H) | 343 |
| 50[16] | 4-(trifluoromethyl)benzyl-ethyl | 8.10 (d, 1H), 7.62 (d, 2H), 7.45 (d, 2H), 7.18–6.98 (m, 3H), 3.90 (m, 1H), 3.74 (m, 4H), 2.83–2.64 (m, 6H), 2.04 (m, 2H), 1.86 (m, 2H), 1.76 (m, 2H), 1.64 (m, 2H) | 389 |
| 51 | CH2Ph | 7.78 (d, 1H), 7.37–7.20 (m, 5H), 7.17–7.02 (m, 3H), 3.88 (m, 1H), 3.64 (s 2H), 2.85–2.63 (m, 10H), 2.00 (m, 2H), 1.76 (m, 2H) 1.62 (m, 2H) | 321 |

[1] The product was not purified by column chromatography
[2] The reaction was carried out by heating in a 40° C. oil bath for 16 hours.
[3] The solvent used for column chromatography was 25% methanol in methylene chloride.
[4] The solvent used for column chromatography was 25% ethyl acetate in hexane.
[5] The reaction was carried out at room temperature for 3 days.
[6] The crude product was purified by the following procedure. The crude product was dissolved in diethyl ether and washed with 1M NaOH and then saturated NaCl. The organic layer was then dried over anhydrous MgSO$_4$, filtered and concentrated to give the product.
[7] The solvent used for column chromatography was 50% ethyl acetate in hexane.
[8] The reaction was carried out by heating in a 60° C. oil bath for 16 hours followed by stirring at room temperature for 16 hours.
[9] The reaction was carried out by heating in a 70° C. oil bath for 16 hours.
[10] The solvent used for column chromatography was 5% methanol im methylene chloride.
[11] The reaction was carried out by heating in a 60° C. oil bath for 2 days followed by stirring at room temperature for 2 days.
[12] The solvent used for column chromatography was a gradient from 25% to 50% ethyl acetate in hexane.
[13] The reaction was carried out by heating in a 70° C. oil bath for 2 days.
[14] The solvent used for column chromatography was 2.5% methanol in methylene chloride.
[15] The solvent used for column chromatography was 1% methanol in diethyl ether:hexane (1:1).
[16] The reaction was carried out by heating in a 70° C. oil bath for 4 hours followed by stirring at room temperature for 16 hours.
[17] The solvent used for column chromatography was 20% diethyl ether in hexane.
[18] The solvent used for column chromatography was 15% diethyl ether in hexane.
[19] The reaction was carried out by heating in a 50° C. oil bath for 2 hours followed by stirring at room temperature for 16 hours.

EXAMPLE 52

R 1-(1,2,3,4-Tetrahydronaphthyl)-4-(2-methylpropyl)homopiperazine

A 50 mL flask was charged with R 1-(1,2,3,4-tetrahydronaphthyl)-homopiperazine (1.12 g, 4.85 mmol) and isobutyric acid (12.8 g, 145 mmol). The flask was immersed in a 50° C. oil bath. After heating for 10 minutes, NaBH$_4$ was added in portions over 15 minutes. After heating for 16 hours, the resulting mixture was immersed in an ice water bath and water (20 mL) was added. NaOH pellets were added until the solution was strongly basic. The mixture was then extracted with ethyl acetate (3×125 mL) and the combined extracts were dried over anhydrous MgSO$_4$, filtered and concentrated to give a yellow oil. This crude product was purified by simple distillation under reduced pressure using a short-path distillation apparatus (bp=121–126° C., 120 mtorr) to obtain the title compound as a colorless oil (1.19 g). $^1$H NMR (CDCl$_3$, 300 MHz) δ 0.89 (d, 6H), 1.58–1.76 (m, 5H), 1.93–2.08 (m, 2H), 2.24 (d, 2H), 2.59–2.77 (m, 10H), 3.86 (m, 1H), 7.02–7.18 (m, 3H). 777 (d, 1H); m/s: M+H$^+$ 287.

EXAMPLES 53–57

By the method of Example 52, substituting the corresponding acid compound for isobutyric acid the following compounds were prepared, wherein (R) and (S) refer to the stereochemistry at the 1-position of the 1,2,3,4-tetrahydronaphthyl ring.

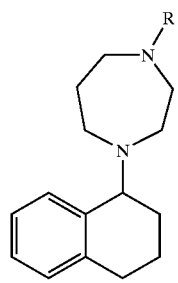

| Example | R¹ | NMR | m/s M + H⁺ |
|---|---|---|---|
| 53 | (S) <br> isobutyl | 0.88 (d, 6H), 1.58–1.76 (m, 5H), 1.93–2.08 (m, 2H), 2.24 (d, 2H), 2.60–2.76 (m, 10H), 3.88 (m, 1H), 7.02–7.18 (m, 3H), 7.78 (d, 1H) | 287 |
| 54 | (R) —Et | 1.07 (t, 3H), 1.58–1.68 (m, 2H), 1.70–1.80 (m, 2H), 1.93–2.08 (m, 2H), 2.54–2.81 (m, 12H), 3.89 (m, 1H), 7.03–7.18 (m, 3H), 7.77 (d, 1H) | 259 |
| 55 | (S) —Et | 1.07 (t, 3H), 1.58–1.68 (m, 2H), 1.71–1.80 (m, 2H), 1.94–2.09 (m, 2H), 2.54–2.81 (m, 12H), 3.89 (m, 1H), 7.03–7.18 (m, 3H), 7.77 (d, 1H) | 259 |
| 56 | (R) -n-Pr | 0.88 (t, 3H), 1.44–1.56 (m, 2H). 1.59–1.71 (m, 2H), 1.72–1.82 (m, 2H), 1.93–2.08 (m, 2H), 2.43–2.48 (m, 2H), 2.62–2.80 (m, 10H), 3.88 (m, 1H), 7.02–7.18 (m, 3H), 7.77 (d, 1H) | 273 |
| 57 | (S) -n-Pr | 0.88 (t, 3H), 1.43–1.56 (m, 2H), 1.58–1.70 (m, 2H), 1.70–1.81 (m, 2H), 1.93–2.08 (m, 2H), 2.43–2.48 (m, 2H), 2.60–2.80 (m, 10H), 3.88 (m, 1H), 7.02–7.18 (m, 3H), 7.77 (d, 1H) | 273 |

EXAMPLE 58

Following conventional procedures well known in the pharmaceutical art the following representative pharmaceutical dosage forms containing a compound of formula I can be prepared:

| (a) Tablet | mg/tablet |
|---|---|
| Compound of Formula 1 | 50.0 |
| Mannitol, USP | 223.75 |
| Croscarmellose sodium | 60 |
| Maize starch | 15.0 |
| Hydroxypropylmethylcellulose (HPMC), USP | 2.25 |
| Magnesium stearate | 3.0 |

| (b) Capsule | mg/capsule |
|---|---|
| Compound of Formula 1 | 10.0 |
| Mannitol, USP | 488.5 |
| Croscarmellose sodium | 15.0 |
| Magnesium stearate | 1.5 | c) Injection

For intravenous administration, a compound of Formula I is dissolved in an isotonic sterile solution (5 mg/ml).

What is claimed is:

1. A compound of the formula (I)

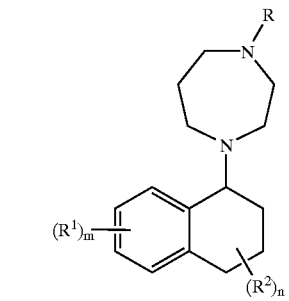

wherein

R is hydrogen, $C_{1-10}$alkyl, $C_{3-8}$cycloalkyl, $C_{3-8}$cycloalkyl$C_{1-6}$alkyl, phenyl$C_{1-6}$alkyl or phenyl;

$R^1$ is $C_{1-6}$alkyl, $C_{2-6}$alkenyl, $C_{1-6}$alkoxy, halo, hydroxy, $C_{1-6}$alkanoyl, halo$C_{1-6}$alkyl, cyano or nitro;

m is 0, 1 or 2;

$R^2$ is $C_{1-6}$alkyl;

n is 0, 1 or 2;

wherein any phenyl ring is optionally substituted;

or a pharmaceutically acceptable salt thereof.

2. A compound according to claim 1 wherein:

R is hydrogen, $C_{1-6}$alkyl, $C_{3-8}$cycloalkyl, $C_{3-8}$cycloalkyl$C_{1-6}$alkyl, phenyl$C_{1-6}$alkyl or phenyl;

$R^1$ is $C_{1-6}$alkyl, $C_{1-6}$alkoxy, halo, hydroxy, halo$C_{1-6}$alkyl, cyano or nitro;

m is 0, 1 or 2;

$R^2$ is $C_{1-6}$alkyl, and n is 0, 1 or 2;

wherein any phenyl ring is optionally substituted.

3. A compound according to claim 1 wherein R is hydrogen or $C_{1-6}$alkyl.

4. A compound according to claim 1 wherein R is phenyl$C_{1-6}$alkyl.

5. A compound of formula (I) according to claim 1 wherein R is hydrogen, $C_{1-6}$alkyl or phenyl$C_{1-6}$alkyl and $R^1$ is hydrogen or $C_{1-6}$alkoxy.

6. A compound according to claim 1 wherein the chiral centre at the 1-position of the 1,2,3,4-tetrahydronaphthalene ring has S-stereochemistry.

7. A compound according to claim 1 selected from:
- (R) 1-methyl-4-(1,2,3,4-tetrahydro-1-naphthalenyl)homopiperazine;
- (S) 1-methyl-4-(1,2,3,4-tetrahydro-1-naphthalenyl)homopiperazine;
- (R) 1-ethyl-4-(1,2,3,4-tetrahydro-1-naphthalenyl)homopiperazine;
- (S) 1-ethyl-4-(1,2,3,4-tetrahydro-1-naphthalenyl)homopiperazine;
- 1-propyl-4-(1,2,3,4-tetrahydro-1-naphthalenyl)homopiperazine;
- 1-propyl-4-(1,2,3,4-tetrahydro-1-naphthalenyl)homopiperazine;
- (R) 1-isopropyl-4-(1,2,3,4-tetrahydro-1-naphthalenyl)homopiperazine;
- (S) 1-isopropyl-4-(1,2,3,4-tetrahydro-1-naphthalenyl)homopiperazine;
- (R) 1-(2-methylpropyl)-4-(1,2,3,4-tetrahydro-1-naphthalenyl)homopiperazine;
- (S) 1-(2-methylpropyl)-4-(1,2,3,4-tetrahydro-1-naphthalenyl)homopiperazine;
- 1-(3-methylbutyl-4-(1,2,3,4-tetrahydro-1-naphthalenyl)homopiperazine;
- 1-(3-methylbutyl-4-(1,2,3,4-tetrahydro-1-naphthalenyl)homopiperazine;
- (R) 1-(2-phenethyl)-4-(1,2,3,4-tetrahydro-1-naphthalenyl)homopiperazine;
- 1-(2-phenethyl-4-(1,2,3,4-tetrahydro-1-naphthalenyl)homopiperazine;
- (R) 1-(3-phenylpropyl-4-(1,2,3,4-tetrahydro-1-naphthalenyl)homopiperazine, and
- 1-(3-phenylpropyl)-4-(1,2,3,4-tetrahydro-1-naphthalenyl)homopiperazine.

8. A process for preparing a compound of the formula (I)

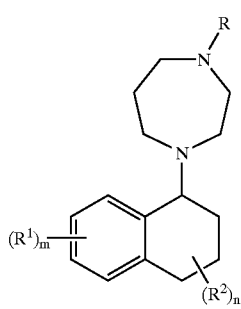

(I)

or a pharmaceutically acceptable salt thereof, wherein

R is hydrogen, $C_{1-10}$alkyl, $C_{3-8}$cycloalkyl, $C_{3-8}$cycloalkyl$C_{1-6}$alkyl, phenyl$C_{1-6}$alkyl or phenyl;

$R^1$ is $C_{1-6}$alkyl, $C_{2-6}$alkenyl, $C_{1-6}$alkoxy, halo, hydroxy, $C_{1-6}$alkanoyl, halo$C_{1-6}$alkyl, cyano or nitro;

m is 0, 1 or 2;

$R^2$ is $C_{1-6}$alkyl;

n is 0, 1 or 2;

wherein any phenyl ring is optionally substituted, which process comprises:

reacting a compound of formula (III) with a compound of formula (IV):

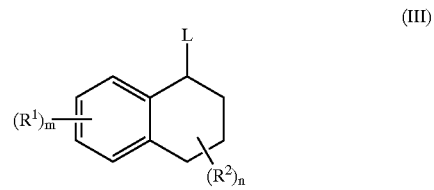

(III)

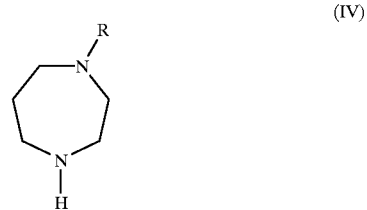

(IV)

wherein L is a leaving group; or deprotecting a compound of formula (V):

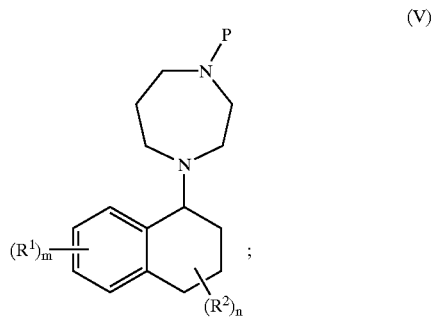

(V)

wherein P is a protected group R;

wherein any functional group is protected, if necessary, and:

removing any protecting groups;

optionally converting a compound of formula (I) into another compound of formula (I);

optionally forming a pharmaceutically acceptable salt.

9. A pharmaceutical composition which comprises a compound according to claim 1 and a pharmaceutically acceptable carrier.

10. A method of treating an ischemia-caused neurological disorder wherein inhibition of the [$^3$H]-emopamil binding site is beneficial which comprises administering to a patient in need thereof an effective amount of a compound according to claim 1.

11. A method of treating an ischaemia-caused neurological disorder selected from stroke, head trauma and transient cerebral ischemic attack which comprises administering to a patient in need thereof an effective amount of a compound according to claim 1.

* * * * *